US010918486B2

(12) United States Patent
Amis et al.

(10) Patent No.: US 10,918,486 B2
(45) Date of Patent: *Feb. 16, 2021

(54) IMPLANT AND IMPLANT SYSTEM

(71) Applicant: Imperial Innovations, Ltd., London (GB)

(72) Inventors: Andrew Arthur Amis, London (GB); Justin Peter Cobb, London (GB); Anthony Michael James Bull, London (GB); Sarat Babu, Danbury (GB)

(73) Assignee: Imperial Innovations, Ltd., London (GB)

(*) Notice: Subject to any disclaimer, the term of this patent is extended or adjusted under 35 U.S.C. 154(b) by 0 days.

This patent is subject to a terminal disclaimer.

(21) Appl. No.: 16/036,201

(22) Filed: Jul. 16, 2018

(65) Prior Publication Data

US 2018/0318090 A1 Nov. 8, 2018

Related U.S. Application Data

(63) Continuation of application No. 15/053,469, filed on Feb. 25, 2016, now Pat. No. 10,022,230, which is a
(Continued)

(30) Foreign Application Priority Data

Jun. 7, 2011 (GB) ..................... 1109515

(51) Int. Cl.
*A61F 2/30* (2006.01)
*A61F 2/38* (2006.01)
(Continued)

(52) U.S. Cl.
CPC ........ *A61F 2/30756* (2013.01); *A61F 2/3872* (2013.01); *A61B 17/562* (2013.01);
(Continued)

(58) Field of Classification Search
CPC ................ A61F 2/3872; A61F 2/30756; A61F 2002/30754; A61F 2/30749; A61F 2002/30576; A61F 2002/30131; A61F 2002/3895; A61F 2/30965; A61F 2002/30004; A61F 2250/0014;
(Continued)

(56) References Cited

U.S. PATENT DOCUMENTS 4,880,429 A * 11/1989 Stone ........................ A61F 2/28
623/14.12
4,919,667 A 4/1990 Richmond
(Continued)

FOREIGN PATENT DOCUMENTS

EP 0372811 6/1990
WO WO-2009149093 A1 * 12/2009 ........... A61F 2/3872

*Primary Examiner* — David H Willse
*Assistant Examiner* — Javier G Blanco
(74) *Attorney, Agent, or Firm* — Crockett & Crockett, PC; K. David Crockett, Esq.

(57) ABSTRACT

An implant system for implantation at a joint, the implant system including an implant device, the implant device comprising a body portion having first and second ends, and a first elongate member, extending from the first or second end of the body portion, the first elongate member being insertable in a bone tunnel in a subject's tibia.

16 Claims, 11 Drawing Sheets

Related U.S. Application Data continuation of application No. 14/123,918, filed as application No. PCT/GB2012/051284 on Jun. 7, 2012, now Pat. No. 9,283,077.

(51) Int. Cl.
*A61B 17/56* (2006.01)
*A61F 2/46* (2006.01)

(52) U.S. Cl.
CPC ....... *A61F 2/30721* (2013.01); *A61F 2/30749* (2013.01); *A61F 2/30965* (2013.01); *A61F 2/4618* (2013.01); *A61F 2002/30004* (2013.01); *A61F 2002/30014* (2013.01); *A61F 2002/30131* (2013.01); *A61F 2002/30576* (2013.01); *A61F 2002/30754* (2013.01); *A61F 2002/4615* (2013.01); *A61F 2220/0016* (2013.01); *A61F 2230/0013* (2013.01)

(58) Field of Classification Search
CPC ... A61F 2002/30014; A61F 2250/0018; A61B 17/562
USPC .................................. 623/13.14, 14.12, 20.3
See application file for complete search history.

(56) References Cited

U.S. PATENT DOCUMENTS

| | | |
|---|---|---|
| 5,092,894 A | 3/1992 | Kenny |
| 5,171,322 A | 12/1992 | Kenny |
| 5,425,767 A | 6/1995 | Steininger et al. |
| 6,283,996 B1 | 9/2001 | Chervitz |
| 7,591,823 B2 | 9/2009 | Tiperneni |
| 8,771,363 B2 | 7/2014 | Grotz |
| 2003/0036797 A1 | 2/2003 | Malaviya et al. |
| 2004/0117014 A1 | 6/2004 | Bryant |
| 2005/0278025 A1* | 12/2005 | Ku .................... A61F 2/3872 623/14.12 |
| 2007/0100450 A1* | 5/2007 | Hodorek ............... A61L 27/52 623/14.12 |
| 2008/0255665 A1 | 10/2008 | Weissberg |
| 2009/0234453 A1 | 9/2009 | Steinberg |
| 2011/0224791 A1 | 9/2011 | Hodorek et al. |

* cited by examiner

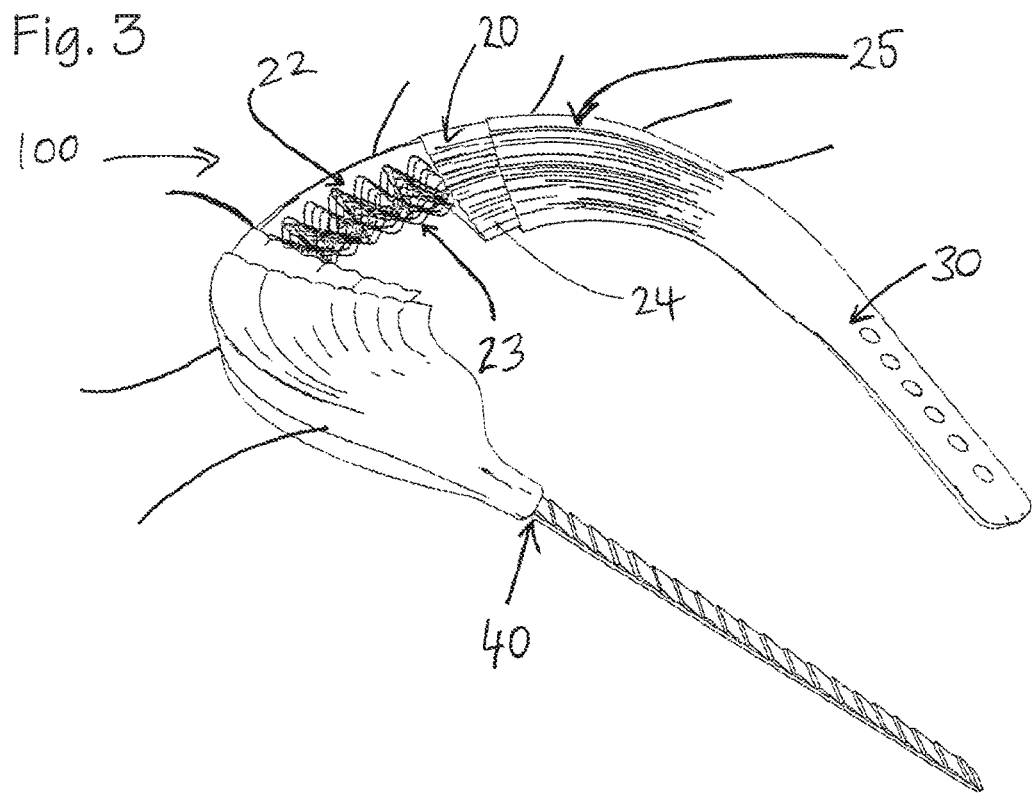
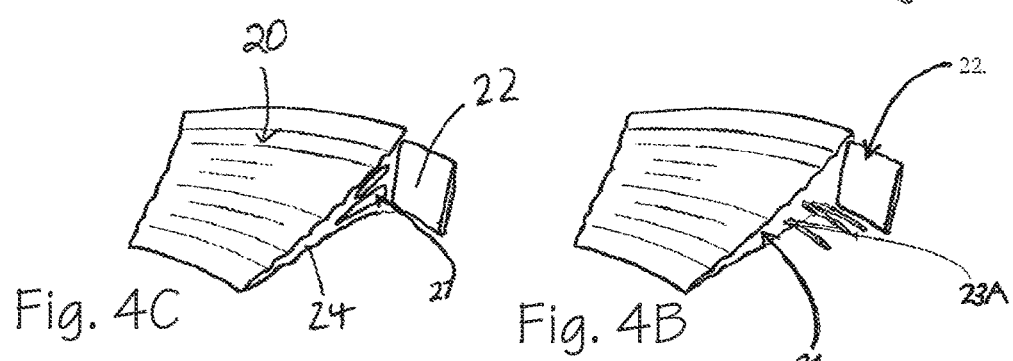
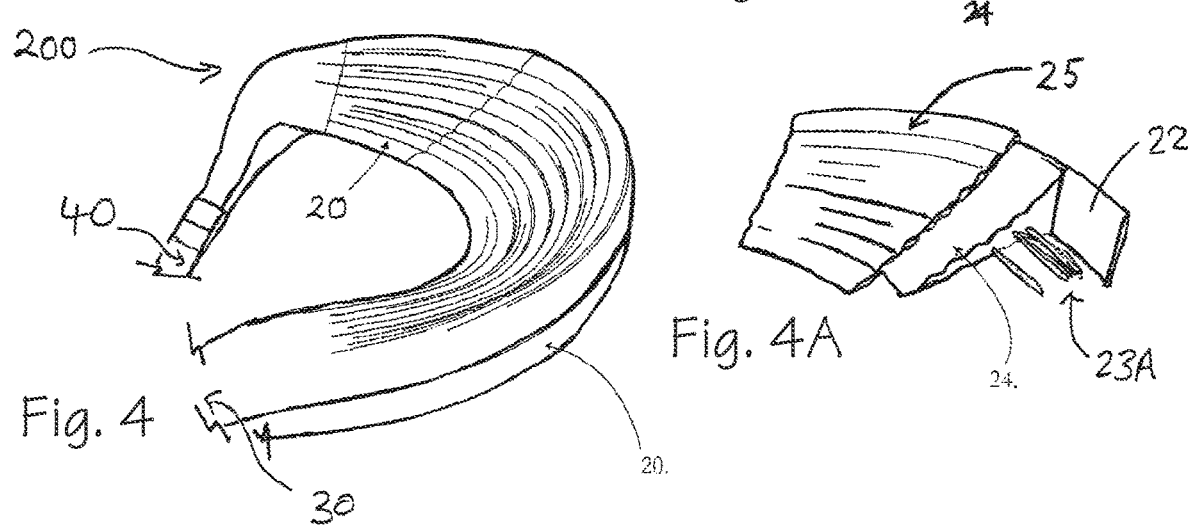

IMPLANT AND IMPLANT SYSTEM

This application is a continuation of U.S. application Ser. No. 15/053,469, filed Feb. 25, 2016, now U.S. patent Ser. No. 10/022,230, which is a continuation of U.S. application Ser. No. 14/123,918, filed Dec. 4, 2013, now U.S. Pat. No. 9,283,077, which is a national stage of PCT Application PCT/GB2012/051284, filed Jun. 7, 2012, which in turn claims priority to Great Britain Patent Application 1109515.5 filed Jun. 7, 2011.

FIELD OF THE INVENTION

The present invention relates to implants and implant systems for implantation in a joint of a human or animal subject.

BACKGROUND TO THE INVENTION

Meniscal injuries account directly for over 50% of all surgery performed on the knee. Tears of the meniscus can occur at any age, but acute tears are most common in the 20 to 40 age group. These tears are more common in men and are often associated with sporting activities, such as tennis and football. Estimates at the incidence of acute tears vary between 24 to 60 per 100,000 population per year (Clayton & Court-Brown 2008, Arendt 1999). Medial meniscal tears occur almost twice as frequently as lateral meniscal tears (Campbell et al. 2001). Increasing age results in degeneration of the meniscal tissue with subsequent tearing. Estimates suggest that 60% of people aged over 65 have a degenerate meniscal tear. Approximately 850,000 meniscal procedures are performed each year in the United States alone (Arendt 1999).

Surgery for meniscal tears, whether acute or degenerate, most commonly involves a partial meniscectomy with resection of the torn region of the meniscus. However, this loss of meniscal tissue is now fully appreciated to increase the probability of developing degenerative changes in the joint and accelerate the degeneration in joints with pre-existing osteoarthritis (Hede et al. 1992, Andriacchi et al. 2004, Hunter et al. 2006, Roos 2005, Roos et al. 1995), therefore resulting in poor outcome (McDermott & Amis 2006). Consequently the desire is to repair or replace the meniscus to retain its function. Meniscal repair is an established procedure, but is only effective for a limited number of tears found solely in the periphery of the meniscus (Heckmann et al. 2006). Attempts to regenerate meniscal tissue using scaffolds have thus far failed to completely restore meniscal volume and are reliant on the presence of an intact peripheral rim of meniscus (Schonenfeld et al. 2007). Meniscal transplantation from cadaveric donors is an established technique (Verdonk et al. 2005) which is limited by a lack of supply, risk of infection and difficulty sizing the donor meniscus to the recipient. Clinical results at over 10 years show encouraging improvement in symptoms, and delay in progression of osteoarthritic radiographic signs but meniscal extrusion is seen in almost all cases (Van der Wal et al. 2009, Verdonk et al. 2006). While the procedure requires patients to be matched to donors, issues of sizing and compatibility will contribute to the variation in results seen (Ha et al. 2010, Lee et al. 2010).

Scaffold developers Regen Biologics and Orteq have estimated the potential value of the global meniscus market at $1.6 and $2 billion respectively based on replacing 50% of the 1.4-1.5 million partial meniscectomies estimated to be performed worldwide each year (ReGen Biologics 2009, Tan 2008).

Functional Role of the Meniscus

The menisci are two crescentic, wedge-shaped fibrocartilages lying on the tibial plateau in the medial and lateral compartments of the knee. They are attached to the underlying bone (tibia) via insertional ligaments at their anterior and posterior horns. Their primary roles are to distribute loading across the joint and to provide passive stability across the range of joint motion (Bullough et al. 1970, Seedhom 1976, Kurosawa et al. 1980, Markolf 1981, Levy 1989). Meniscal material is composed of about 75% water, about 20% type I collagen fibres and about 5% non-collagenous substances (McDevitt & Webber 1990, Wirth 1996). Therefore the tissue is naturally inhomogeneous and composite. Meniscal microstructure comprises predominantly of a dense framework of circumferentially orientated collagen fibre-bundles, with additional randomly orientated fibres tying the circumferential bundles together (Petersen & Tillman 1998). This complex arrangement means that the meniscus is locally anisotropic, providing stiffness in the circumferential direction.

Shape, structure and attachments of the menisci combine to support the primary load bearing functional role of the tissue (Masouros et al. 2008). When the femur bears down onto the tibia (so when the knee joint bears load), the knee joint is subjected to compression. The compressive force is distributed across the joint over an articulating contact area, resulting in contact stresses (contact pressure). These stresses are proportional to the load and inversely proportional to the contact area; in other words, the larger the contact area over which the load is distributed the less the contact stress. However, the geometry of the bony surfaces that articulate at the knee joint are not conforming fully, and therefore do not minimise contact stresses on the underlying articular cartilage. The menisci optimise the way the load is transferred through the joint by increasing the conformity of the articulation; as the femur bears down onto the tibia, the wedged cross-section of the menisci causes them to extrude radially out of the joint; this causes their circumference to increase. The meniscal structure resists this radial displacement by developing tension along its strong circumferentially orientated fibre-bundles (hoop stresses); this tension is then transferred through the insertional ligaments at the meniscal horns into the tibia. This load bearing mechanism occurs throughout the whole range of knee motion, as the menisci are mobile structures, able to conform to the articulating surfaces at any knee-joint position; this is precisely because the menisci are mainly attached to the tibia via insertional ligaments at their horns.

Existing Meniscal Replacements

Prior art has attempted to replace the meniscal tissue through either a scaffold system or a synthetic replacement. Scaffolds are intended to replace tissue removed during a partial menisectomy. They involve the use of a porous material which is usually sutured to the remaining meniscal tissue in the hope that tissue ingrowth will occur through the scaffold. Results have shown, however, that due to poor vascularisation in the main body of the meniscus these scaffolds are not successful in promoting regrowth; due to shrinkage, they often fail to replace the entire lost volume of tissue. Therefore, their long-term ability to reconstruct a functional meniscus remains elusive. Synthetic replacements have been attempted involving various hydrogel materials, in order to improve the general material properties of the prosthetic. However, few of these synthetic prosthetics provide evidence of effective load bearing or mechanical simulation of the meniscus.

SUMMARY OF THE INVENTION

According to a first aspect of the invention there is provided an implant system for implantation at a joint, the implant system including an implant device, the implant device comprising a body portion having first and second ends, and
a first elongate member, extending from the first or second end of the body portion,
the implant system further comprising a corresponding fixation device for securing the first elongate member to a subject, the fixation device comprising at least one latching element, the first elongate member comprising at least one cooperating element, the at least one cooperating element being capable of cooperating with said at least one latching element of the fixation device in use.

The invention provides a fastening mechanism for fastening said elongate member of the implant device to the subject in use. The first elongate member is a tension member for securing to the subject in use. The cooperating element of the elongate member cooperates with the latching element of the fixation device in use, the latching element and cooperating element suitably providing complementary engagement means that engage with one another in use. The fixation device is adapted for fixation relative to a subject, such that the elongate member can suitably be secured to the subject. The at least one cooperating element may comprise any suitable element such as a ratchet tooth, a ridge of a threaded formation such as a buttress thread or other serrated formation, or an aperture in the elongate member for cooperation with the corresponding latching element. Suitably, the implant device is used as a replacement for natural tissues, including for example, replacement of a meniscus of the knee joint. Suitably, the implant system is adapted to provide direct or indirect fixation of the implant device to biological tissue.

Preferably the implant device comprises a second elongate member extending from the other of the first or second end of the body portion from which the first elongate member extends.

Preferably the implant system further comprises a second corresponding fixation device for securing the second elongate member to a subject, said fixation device comprising at least one latching element, the second elongate member comprising at least one cooperating element, the at least one cooperating element of the second elongate member being capable of cooperating with said at least one latching element of said fixation device in use. Suitably, the second elongate member is a second tension member for securing to the subject in use.

Preferably the first and/or second elongate member is provided with a plurality of cooperating elements, said at least one latching element of the corresponding fixation device being capable of cooperating with any one of the cooperating elements in use. By having a plurality of cooperating elements, the first or second elongate member can be drawn to a desired tension and said at least one latching element of the fixation device can be engaged with the cooperating element that provides the desired tension in said elongate member, such that the elongate member can be secured to the subject under a desired tension.

Preferably the cooperating elements of said plurality of cooperating elements are spaced apart from one another along at least a portion of the length of the elongate member. By providing a plurality of cooperating elements spaced along the elongate member at discrete positions, the tension exerted on the implant device when secured to the subject can be varied by varying the cooperating element with which the at least one corresponding latching element engages in use.

The first and/or second fixation device may comprise a plurality of latching elements, each being capable of cooperating with said at least one cooperating element of the corresponding elongate member. The latching elements of said plurality of latching elements may be spaced apart from one another along at least a portion of a length of said fixation device.

Preferably said at least one latching element and said at least one cooperating element comprise a ratchet mechanism.

Preferably the ratchet mechanism comprises at least one ratchet element and at least one ratchet stop, the at least one ratchet element being capable of cooperating with the at least one ratchet stop in use. Suitably the at least one cooperating element may be a ratchet element and the at least one latching element may be a ratchet stop.

The cooperating ratchet element and ratchet stop providing a ratchet-like fixation means, which the installer can use to adjust fixation, to optimise the load-bearing function of the implant device. The use of a ratchet mechanism for fixation of the implant device helps to maintain the ability of the implant device to transmit pressure/compressive loads to the subject's body. The fixation means helps to prevent the fixation from moving or relaxing after implantation, in response to the cyclic loads imposed in use. The fixation means also allows for optimised tensioning of the implant device during implantation and during subsequent revision procedures to re-tension the implant device if desired. Suitably the ratchet type mechanism allows movement of the elongate member relative to the fixation device in one direction but not in the opposing direction, such that the implant device is easy to fit and adjust, but can be securely fixed to the subject once implanted.

Preferably the first and/or second elongate member has a plurality of ratchet teeth. For example, the first or second elongate member may comprise a barbed plate or similar. Alternatively, the first and/or second elongate member may have a plurality of apertures provided as ratchet elements, to cooperate with the at least one ratchet stop on the corresponding fixation device.

Preferably the first and/or second elongate member terminates in a free end.

Preferably each ratchet tooth comprises a first surface angled relative to said elongate member, the first surface sloping towards said elongate member in a direction towards the free end of said elongate member, and a second surface, which slopes towards said elongate member in a direction away from the free end of said elongate member, said second surface being more steeply sloped than said first surface.

Preferably at least a portion of the first and/or second elongate member is strap shaped. For example, the elongate member(s) may be flat, planar members that are tape-like, ribbon-like or belt-like or similar.

Preferably at least a portion of the first and/or second elongate member is substantially crescent shaped in cross-section. In this case, the concave side of the crescent cross-sectioned portion of the elongate member can be curved to substantially correspond to curvature of the fixation device, and the convex side of the elongate member can be shaped to fit against the curved side wall of a tunnel in the subject's bone for receiving the elongate member. Said elongate element may have a plurality of cooperating elements on the concave side for cooperating with the at least one latching element of the fixation device. Said elongate member may also have fixation means on the convex side for engaging with the bone. The fixation means may be, for example a plurality of ridges such as teeth.

Preferably the first and/or second fixation device is adapted to be secured to a subject's bone in use.

Preferably the first and/or second fixation device is securable to a subject's bone, said fixation device having a lower face that faces towards the bone when secured to the subject's bone, the device having at least one latching element on its lower face for cooperating with said corresponding cooperating element in use.

Preferably said fixation device is shaped to provide a channel between the lower face and the bone when said fixation device is secured to a subject's bone, the elongate member being insertable within the channel in use.

Suitably, the ratchet mechanism allows the elongate member to be moved through the channel in one direction (i.e. to tighten the implant device) but not the other direction. For example, the elongate member may have a serrated surface or a plurality of apertures, the fixation device being a staple bridging over the elongate member in use and including a serrated and/or spiked surface on the underside of the crossbar of the staple, to engage the serrations and/or plurality of apertures in the elongate member, providing a ratchet type mechanism allowing movement of the elongate member relative to the fixation device in one direction but not in the opposing direction. Suitably the ratchet type mechanism can be used to tense and re-tense the implant device. The staple-like fixation device may have holes for receiving screws on either side of the crossbar, to secure the fixation device to the subject's bone.

Preferably the system includes means for fixing the fixation device to the bone. Preferably said fixation device is adapted to be screwed or stapled to bone.

Preferably the first and/or second fixation device is externally threaded, the threading forming a plurality of latching elements capable of cooperating with said at least one cooperating element of the corresponding elongate member. Suitably, the threading forms a plurality of ratchet stops capable of cooperating with said at least one ratchet element of the corresponding elongate member.

Preferably the fixation device is a screw, the screw being externally helically threaded.

Preferably the first and/or second elongate member is insertable in a tunnel in a subject's bone, the tunnel having first and second open ends, the corresponding fixation device being insertable in the second end of the tunnel, such that the at least one latching element of said fixation device engages with the at least one cooperating element on said elongate member, the corresponding fixation device being securable non-movably relative to the tunnel, preventing the elongate member from being withdrawn from the tunnel via the first open end.

Preferably the implant system further comprises an elongate sheath, the first or second elongate member being insertable in the sheath. The sheath may be receivable in a tunnel formed in the subject's bone Preferably the sheath has means for non-movably securing it to a subject's bone. Preferably the sheath has means for non-movably securing it within a tunnel formed in a subject's bone. Preferably the sheath has a first end and a second end, either or both of the first and second ends having two or more longitudinal cuts therein, forming arms in said end of the sheath, wherein said arms are biased apart from one another in use. Suitably the arms flare/splay apart, and push against bone in use, lodging the sheath in the bone.

Preferably the corresponding fixation device is insertable in the sheath. Suitably, the sheath has first and second ends, the elongate member being insertable via the first end and the fixation device being insertable via the second end.

Preferably the internal surface of the sheath has at least one protuberance capable of cooperating with said at least one latching element on the corresponding fixation device.

Preferably at least a portion of the sheath is internally screw threaded, said fixation device being correspondingly externally threaded, such that said fixation device is capable of securely engaging in the sheath.

By non-movably securing the sheath to the bone and inserting the elongate member in the sheath, the elongate member can be secured relative to the bone, by securing it to the elongate member. This allows for easy exchange of the implant device, for example if the implant device material has worn away, without the need for re-drilling/re-cutting in the subject's bone.

Preferably the first elongate member is insertable in a first tunnel in a subject's bone and the second elongate member is insertable in a second tunnel in a subject's bone, the second elongate member being provided with at least one cooperating element, the fixation device being adapted to secure both the first and second elongate members to the subject, the fixation device comprising at least a first latching element for cooperating with the at least one cooperating element of the first elongate member and the fixation device further having at least a second latching element for cooperating with the at least one cooperating element of the second elongate member in use. Suitably, when being implanted at the knee, both elongate members pass through corresponding bone tunnels to similar places on the surface of the tibia, wherein the two ends of the elongate members may be folded over one another and secured by the single fixation device onto the surface of the tibia. The fixation device may include ratchets stops facing in first and second directions, for cooperating with ratchet elements on the first and second elongate members respectively.

Preferably the implant device further comprises a reinforcing element, which extends through the first elongate member and through the body portion of the implant device. Suitably the reinforcing element extends continuously (i.e. its length is unbroken) through the first elongate member and through the body portion of the implant device. The reinforcing element acts as a tension member extending through the implant device.

Preferably the reinforcing element extends through the first elongate member, through the body portion of the implant device, and through the second elongate member. Suitably the reinforcing member is embedded within the body portion, or may be at its outer surface, and within the elongate member(s). Suitably, the elongate member may have a higher modulus of elasticity than that of the body portion. In this way, the elongate member is sufficiently stiff in order to be pushed/inserted into a fixation tunnel or channel.

Preferably the elongate element is strap shaped.

Preferably said at least one cooperating element of the first and/or second elongate member comprises at least one aperture for receiving said latching element of the corresponding fixation device in use, for directly securing said elongate member to bone. For example, the fixing means may be a screw. Alternatively, the fixation device may be a cross-pin fixator, adapted to be received in a bone tunnel drilled transverse to a bone tunnel for receiving the elongate member, the cross-pin fixator being adapted to be received though the aperture of the elongate element to secure the elongate element to the subject's bone. In this case, said latching element is the part of the fixation device adapted for passing through the aperture of said elongate member.

According to a further aspect of the invention there is provided an implant device for implantation at a joint, the implant device comprising a body portion having first and second ends, and first and second elongate members, the first elongate member extending from the first end of the body portion and the second elongate member extending from the second end of the body portion, the implant device further having a reinforcing element that extends through the first elongate member, through the body portion of the implant device, and through the second elongate member, the first and second elongate members being adapted for fixation relative to a subject's body.

Suitably, the reinforcing element transfers forces exerted on the body portion of the device to the subject's body in use by means of the elongate members with reinforcing element therein being fixed to the subject's body in use. The reinforcing element extends into the elongate members of the implant device, which are anchored to the body in use, therefore allowing the reinforcing element to transfer mechanical loads exerted on the body portion of the implant during use to the subject's body. The reinforcing element is therefore a tension member. Suitably the reinforcing element is embedded within a polymeric matrix that forms the body portion. Suitably the reinforcing element is also embedded within the polymeric matrix at each of the elongate members, the cross-section of the implant device being smaller in each elongate member than that of the body portion. Suitably the reinforcing element is unitary, in that it forms a single piece that extends through the length of the device, from within the first elongate element, through the body portion, and into the second elongate element. The device may have more than one reinforcing element. Suitably the implant device has first and second means for fixing the first and second elongate members to the subject's bone respectively. The first and second elongate members may be adapted to be fixed to a subject's body directly or indirectly.

The implant device is used as a replacement for natural tissues, including for example, replacement of the menisci of the knee joint. The implant device has the ability to accurately mimic the mechanical behaviour of the native tissue. The implant device comprises a hybrid material having two or more constituents, which through their geometrical arrangement within the implant device are able to create a heterogeneous structure similar to those native tissues that it is designed to replace. The implant device is able to provide improved biomechanical behaviour compared to prior art implant devices.

Preferably the implant device includes fixing means for securing the first and second elongate members to a subject's body.

According to a further aspect of the invention there is provided an implant device for implantation at a joint, the implant device comprising a body portion having first and second ends, and first and second elongate members, the first elongate member extending from the first end of the body portion and the second elongate member extending from the second end of the body portion, the implant device being made from a functionally graded material, having at least one mechanical property that varies spatially with respect to the implant device.

Preferably the body portion is substantially crescent shaped. Preferably the implant device has at least one mechanical property that varies in a radial direction relative to the crescent shaped body portion and/or in a circumferential direction relative to the implant device.

The at least one mechanical property may for example be elastic modulus, tensile stress and/or shear stiffness.

Suitably, the implant device comprises a synthetic tissue with material properties that vary spatially within the device. The implant device exhibits a spatial graded change in the magnitude of one or more physical property. The implant device may comprise a hybrid functionally graded material comprising at least two material ingredients that are varied geometrically in their arrangement to vary localised material properties. Freeform production processes may be used to manufacture the implant device in order to produce a device having properties that vary spatially.

Suitably the form of the implant device replicates that of the native tissue that it is designed to replace with the inclusion of one or more fixation adaptations to the device which assist or are capable of achieving fixation relative to a subject's body.

The term 'circumferential direction' as used herein refers to a direction extending along the axis of the first elongate member, along a path substantially parallel with the circumference of the crescent shaped body portion, and along the axes of the first and second elongate members. Where the body portion is crescent shaped, the circumferential direction would be a curved axis, substantially parallel with the outer rim of the crescent shaped body portion.

Preferably the implant device further comprises a reinforcing element that extends through the first elongate member, through the body portion of the implant device, and through the second elongate member, the first and second elongate members being adapted for fixation relative to a subject's body.

Preferably the reinforcing element is an elongate element.

Preferably the reinforcing element is strap shaped.

Preferably the body portion is substantially crescent shaped, having an arcuate outer rim. The crescent shaped body portion could also be described as arc shaped or shaped like a segment of a circle, with the first and second elongate members extending from the end points Preferably the reinforcing element extends along, or close to and substantially parallel with, the arcuate outer rim of the body portion of the device.

Preferably a planar face of the strap shaped reinforcing element is substantially perpendicular to the transverse plane of the body portion of the device in use. The transverse plane of the device is parallel with the transverse plane of the knee when it is implanted at the knee.

Preferably the implant device further comprises a structural element comprising a plurality of fibres embedded within the body portion.

Preferably at least a portion of each of the fibres extends through the body portion.

Preferably each of the fibres extends through the first elongate member, through the body portion of the implant device, and through the second elongate member.

Preferably each of the fibres is coupled to the reinforcing element at least one point along the length of said fibre. Preferably each of the fibres is coupled to the reinforcing element at two or more points along the length of said fibre.

Preferably the plurality of fibres are arranged such that each fibre crosses over at least one other fibre.

Preferably when the implant device is not subjected to any external forces, the fibres are arranged substantially parallel with the arcuate outer rim of the body portion or, if straight, as chords of the circle formed by the outer rim of the body portion.

Preferably when the implant device is not subjected to any external forces, at least a portion of each fibre is arranged in wave like formation. The wave like arrangement of each fibre suitably has crests and troughs.

Preferably at least a portion of each fibre extends between the posterior and anterior ends of the body portion in a sinusoidal shaped formation.

Preferably the plurality of fibres comprises at least one electrospun anisotropic polymer sheet.

Preferably the body portion is made of or includes a functionally graded material.

Preferably the body portion has an elastic modulus gradient, the elastic modulus varying spatially within the body portion. For example, the body portion may be manufactured from two elastomers via a singular injection casting, producing a continuous gradient or transition of material properties.

Preferably the elastic modulus increases in a radial direction, towards the arcuate outer rim of the body portion.

Preferably the elastic modulus increases in a circumferential direction towards free ends of the first and second elongate members.

Preferably the elastic modulus increases towards the outer surface of the body portion.

Preferably the body portion has a high tensile stiffness along an axis substantially parallel with the outer rim of the body portion, preferably in the range to 50 MPa to 2 GPa and low shear stiffness in a plane substantially transverse to the outer rim of the body portion, preferably in the range 2 to 50 MPa. In other words, the body portion has a low shear stiffness in a plane parallel with a radial axis of the body portion.

Preferably the body portion has a higher tensile stiffness along an axis substantially parallel with the outer rim of the body portion than the shear stiffness in a plane substantially transverse to the outer rim of the body portion.

Preferably the reinforcing element has at least one securing fibre anchored thereto and extending away from the body portion of the implant device. The securing fibres may be used to fix the body portion to the subject, to provide additional fixation that may be temporary or permanent. The securing fibres preferably emerge from the periphery of the body portion, to be used for surgical insertion and/or fixation. The securing fibres may be formed into sutures, which may have needles or soft tissue fixation devices such as toggles mounted on their ends, so that, if implanting at the knee, the sutures may pull the implant device into the back of the knee and then secure it against the capsule there.

Preferably the body portion has at least one area adapted for tissue ingrowth. In order to encourage fixation of the body portion of the implant device with the surrounding joint capsular tissues, at least a portion of the implant device may be provided with tissue ingrowth zones. For example, at least a portion of the implant device may be provided with a textile like outer surface, for promoting soft tissue attachment. At least a portion of the implant device could be moulded with textiles, such as those used in arterial grafts and heart valves. The textile could, for example, have a looped structure, akin to velour, so that the loops on the inner side are moulded into or otherwise adherent to the implant device, while the loops on the outer side will allow tissue ingrowth to the velour-like material. These tissue ingrowth zones may have variable extent, depending on which areas are desired to be fixed to the surrounding tissues. For example, it is desirable that some zones remain unattached, to aid mobility during knee movements, while it is desired that tissue adhere to other zones. Suitably, the mechanical behaviour of the implant device under load may promote integration via tissue growth between the device and biological tissue in certain zones and/or may reduce integration via tissue growth between the device and biological tissue in other zones, for example in the entrances of the bone tunnels which accommodate the fixation means. Suitably a portion of the surface of the body portion may be adapted for tissue ingrowth, in order to stimulate peripheral fixation of the device.

Preferably the body portion has a top face and a bottom face, the top face being substantially concave and the bottom face being substantially flat or substantially concave. Where the implant device is for implantation at the knee, the top face faces the femur when implanted and the bottom face faces the tibia when implanted. The cross-sectional shape of the body portion may vary along a circumferential axis of the body portion. In particular, the radius of curvature of the top face may vary along a circumferential axis of the body portion.

According to a further aspect of the invention there is an implant system according to the first aspect of the invention described above incorporating an implant device having the features of the implant device according to further aspects of the invention.

Preferably the implant system is for implantation at a subject's knee joint, one of the first and second elongate members being a posterior insertion for securing at a posterior region of the subject's tibia and the other of the first and second elongate members being an anterior insertion for securing at an anterior region of the subject's tibia in use. According to a further aspect of the invention, the implant system is a prosthetic meniscus implant system.

A kit can be provided comprising an implant system having a set of implant devices according to any preceding claim wherein the implant devices are provided in a range of sizes. This allows the device to be optimised for the exact dimensions of the individual patient, by selecting the device that ensures optimal fit with the particular patient. The devices can be provided with a set of rules that assist in selection of a suitable implant from the implant set based on the patient's dimensions.

The system can be supplied with a detailed operative plan for the positioning of bony attachments and tunnels, that can be achieved by the use of patient specific drill guides, or the use of surgical navigation or robotic assistance.

According to a further aspect of the invention there is provided a method of implanting an implant system in a subject, the method comprising providing an implant system according to any of the previous aspects of the invention, securing the implant device of the implant system to a subject at a first fixation point, exerting a predetermined tension on the first elongate member, engaging the at least one cooperating element of the first elongate member with the at least one latching element of the corresponding fixation device such that the first elongate member can be secured to the subject at a predetermined tension. The fixation device can be secured to the subject before or after engaging the at least one cooperating element with the latching element.

For example, the fixation device may be a cross-pin fixator or an interference screw that passes through an aperture in the first elongate member. The first elongate member may have a plurality of apertures spaced along its length, such that the desired predetermined tension can be achieved.

According to a further aspect of the invention there is provided a method of implanting an implant system in a subject, the method comprising
providing an implant system according to any of the previous aspects of the invention,
engaging the at least one cooperating element of the first elongate member with the at least one latching element of the corresponding fixation device, such that the first elongate member and fixation device can move relative to one another in one direction, but not in the opposite direction.

The method allows for improved fixation of the implant device to maintain the ability of the implant device to transmit pressure/compressive loads to the subject's body. The fixation means also allows for optimised tensioning of the implant device during implantation and during subsequent revision procedures to re-tension the implant device if desired.

According to a further aspect of the invention there is provided a method of tensioning an implant device, the method comprising
providing an implant system according to any of the previous aspects of the invention,
securing the implant device of the implant system to a subject at a first fixation point,
engaging the at least one cooperating element of the first elongate member with the at least one latching element of the corresponding fixation device, such that the first elongate member and fixation device can move relative to one another in one direction, but not in the opposite direction, and
moving the elongate member relative to the fixation device to tension the implant device.

Function of the implant device may depend on correct tensioning of the implant device, such that it fits snugly around the contact area of the femoral condyle and on the tibial plateau. Suitably, the implant device is fixed to the tibia at one fixation end and tensioning means are attached at the other fixation end of the implant device. Once the implant device has been secured to the subject at the first fixation point, the elongate member extending from the other end of the implant device can be secured to a tensiometer and the tension adjusted to obtain a snug fit around the femoral condyle. The elongate member can then be secured with this tense configuration. Suitably the method can be used to tense and re-tense the implant device.

Features mentioned above with any aspect of the invention may be applied in any combination to the other aspects of the invention, as those skilled in the art will appreciate.

BRIEF DESCRIPTION OF THE DRAWINGS

A preferred embodiment of the present invention will now be more particularly described by way of example only with reference to the accompanying drawings, wherein:

FIG. 3 is a perspective view of an implant device, similar to the implant device of FIG. 1, showing the body portion cutaway, revealing a strap, a structural element, a bulk matrix and an overmoulding;

FIG. 4 shows a perspective view of the body portion of an implant device; FIGS. 4A to 4C show perspective views of various embodiments of the body portion of the device of FIG. 4, showing the body portion cutaway to show the constituents of the hybrid functional graded material; FIG. 4A shows a body portion having an overmoulding, strap and structural element comprising a plurality of fibres; FIG. 4B shows a body portion like that of the FIG. 4A embodiment, but without an overmoulding; FIG. 4C shows a body portion like that of the FIG. 4B embodiment, but having cavities and without a plurality of fibres;

DESCRIPTION OF THE PREFERRED EMBODIMENTS

Figure 1:
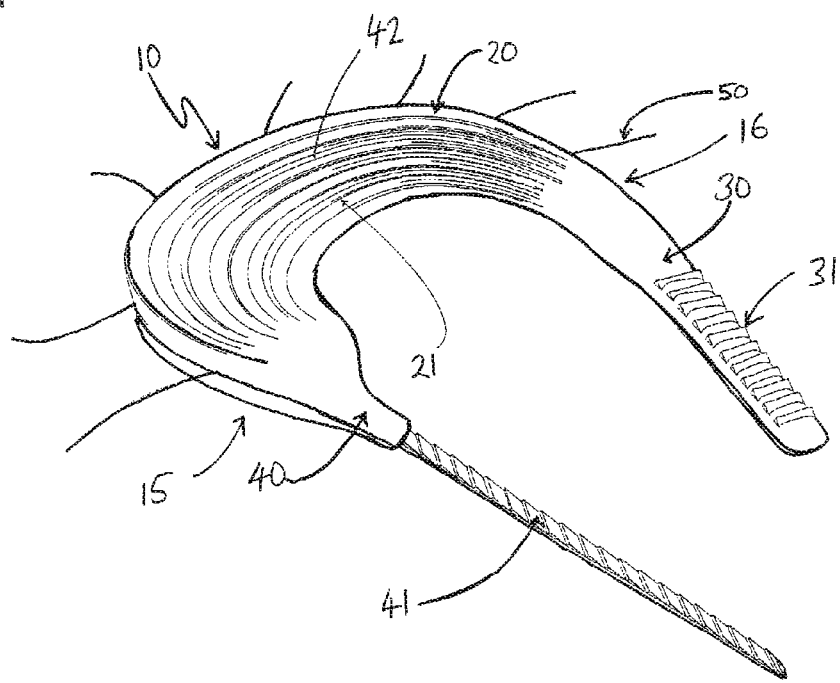
FIG. 1 shows a perspective view of an implant device according to a first embodiment.

The present embodiments represent currently the best ways known to the applicant of putting the invention into practice. But they are not the only ways in which this can be achieved. They are illustrated, and they will now be described, by way of example only. Like reference numerals refer to like parts throughout the drawings.

Referring to FIG. 1, this shows an implant device 10 which may be implanted at the knee as a meniscus prosthesis device. The implant has a body portion 20 shaped approximately as a crescent (i.e. arc shaped or shaped as a segment of a circle), with a substantially wedge shaped cross-sectional shape (i.e. with the outer rim of the body portion being thicker than the inner rim), emulating the shape of natural meniscus tissue in a healthy knee joint. The body portion 20 has a bottom, or tibial face (not visible in FIG. 1), which faces the tibia when implanted and a top, or femoral face 42, which faces the femur when implanted. The body portion 20 has a posterior end 15 and an anterior end 16, corresponding to a subject's posterior and anterior respectively when the implant device is implanted.

The bottom face of the body portion 20 may be substantially flat and the top face 42 may be substantially concave. Alternatively, the body portion 20 may be biconcave (i.e. wherein both the bottom face and top face 42 are concave). In a preferred embodiment the cross-sectional shape of the body portion 20 perpendicular to its transverse plane when implanted varies along the circumferential axis (i.e. the cross-sectional shape varies along an axis substantially parallel with the outer rim of the body portion). In such an embodiment, the bottom face of the body portion 20 may be substantially flat except for a portion at the posterior end of the body portion 20, wherein the bottom face is concave. This embodiment may be particularly useful for replacement of a subject's lateral meniscus. The radius of curvature of the concave top face 42 of the body portion 20 may also be greater towards the posterior and anterior ends of the body portion.

A first elongate member 40 extends from the posterior end 15 and a second elongate member 30 extends from the anterior end 16 of the body portion 20. The first elongate member is a posterior insertion 40 and the second elongate member is an anterior insertion 30 of the implant device 10. The term 'insertion' is used herein to describe the posterior and anterior elongate members, however another term that may be used for these members is 'posterior fixation'/'anterior fixation'; it will of course be understood that the elongate members need not be inserted through any bone tunnel or fixation device in order to secure the posterior and anterior elongate members to the subject, but can be secured to the subject using suitable fixing means. Preferably both the posterior and anterior insertions 40, 30 are flat elongate members, such as a strap (i.e. like a belt or tape) or the like. Alternatively, the anterior and/or posterior insertions 30, 30 may be substantially crescent shaped in cross-section. The concave side of the crescent cross-sectioned portion of the insertion can be curved to substantially correspond to curvature of a fixation device such as a screw, and the convex side of the insertion can be shaped to fit against the curved side wall of a tunnel in the subject's bone for receiving the insertion.

The tibial face and femoral face 42 of the body portion 2 are textured, for example with a plurality of indentations 21, which help to retain liquid from the surrounding area, providing improved lubrication between the device and biological tissue. The texturing of the tibial and femoral faces can also be used to emphasise and vary mechanical properties of the device in relation to the specific requirements in a particular subject's knee joint.

Figure 2:
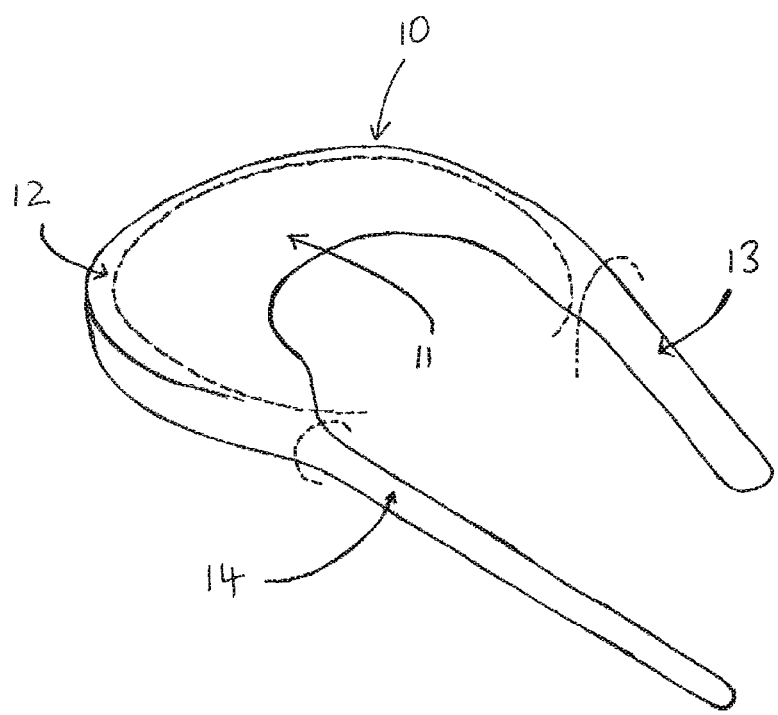
FIG. 2 is a schematic diagram showing a perspective view of an implant device of the present invention, illustrating how gradients of properties of the device may be exhibited in the implant device.

The implant device 10 is a synthetic tissue, which is preferably a hybrid functionally graded material comprising two or more materials, which are geometrically arranged to try to mimic the locally anisotropic properties of the naturally occurring meniscal tissue. Functionally graded materials are so called because their properties have a spatial gradient. Referring to FIG. 2, this schematically shows four different zones that the implant device may have, which have different mechanical properties. Although the schematic diagram in FIG. 2 marks the zones as having discrete boundaries, the boundaries between the zones may also exist as gradients. The implant device body portion 20 has a central portion 11, extending from the inner rim of the body portion to near the outer rim, the central portion 11 being soft in order to conform to deformation from the load of the articular surfaces. The body portion has a peripheral portion at its outer rim, which should be much stiffer, to prevent the central portion 11 from being displaced from the articular surfaces. Extending from the posterior and anterior ends of the outer rim 12 are a posterior insertion portion 14 and anterior insertion portion 13. The posterior insertion portion 14 and anterior insertion portion 13 are exceptionally stiff, and are adapted to secure the device to bone, while allowing the device to biomechanically simulate the movement of the natural tissue.

The implant device 10 preferably features three-dimensional gradients of elastic and shear moduli. The elastic modulus throughout the device should approximate values measured in the natural meniscus, such as between 2 GPa and 2 MPa.

The three-dimensional gradient is created by arranging the constituent materials of the device such that when a localised volume is analysed as a whole, the general properties are close to or match those of a natural meniscus. The three dimensional gradient is made up of two material gradients in order to try to mimic the behaviour of the meniscal tissue: a gradient in the radial direction of the crescent shaped implant device and a gradient in the direction of the circumference of the implant device (i.e. in a direction between posterior and interior insertions, including the arc between the posterior and anterior ends of the body portion). In the radial direction of the body portion 20, the central portion 11 preferably has a bulk elastic modulus of around 10 MPa. However, the outer rim 12 should preferably remain stiff in order to stop the meniscal tissue from being displaced from the tibial plateau. A gradient preferably exists along a radial direction of the implant body portion from the outer rim 12 to the inner rim with the average elastic modulus varying from values around or above 50 MPa at the outer rim to around or lower than 2 MPa at the inner rim.

In a circumferential direction, gradients preferably occur where the load bearing body grades to each of the anterior and posterior insertion portions 13, 14. In a circumferential direction, the elastic modulus varies from values of around or above 100 MPa within the anterior and posterior insertion portions 13, 14, to values as low as 10 MPa within the body portion 20.

The elastic modulus gradients are achieved through the unique arrangement of constituent materials. Embedded within the implant device may be a reinforcement structure (such as a polymer structure, for example made of polyetherketone (PEEK) or other high-modulus polymer). The reinforcement structure may vary in its structure along both the circumference of the device and in a radial direction. Other polymers or polymer substitutes may be used for the reinforcement structure, having an elastic modulus within a range of around 80 MPa to 2 GPa.

The reinforcement structure is overmoulded with or embedded within a polymer, preferably an elastomer, which makes up the main bulk of the device. This polymer matrix making up the main bulk of the implant device may be a silicone/polyurethane elastomer (or elastomer substitute preferably with an elastic modulus below around 10 MPa). The matrix polymer may comprise a functionally graded material, manufactured to have an elastic modulus that varies along the radial direction of the device, the circumferential direction of the device, or both.

The polymer matrix core of the implant device may also have an overmoulding of another polymer (preferably an elastomer) with appropriate wear characteristics to form the outer surface of the implant device, for example poly carbonate urethane. The overmoulding can either be carried out as a one or two stage process depending on whether a continuous or discontinuous gradient between materials is to be achieved.

An example of how these elastic modulus gradients can be achieved is shown in an embodiment of FIG. 3, which shows a cutaway through an implant device 100 revealing the hybrid functionally graded material (FGM) structure. The implant device 10 has an outer overmoulding 25 on the surface of the device, made of a super wear-resistant elastomer. Within the overmoulding 25 is a soft elastomer/elastomer foam core 24, which makes up the bulk of the body portion 20 of the device. In FIG. 3, the overmoulding 25 and core 24 are shown cutaway, revealing a reinforcement structure 22, 23 embedded within the core 24. The core 24 effectively forms a matrix in which the reinforcement structure is located. The reinforcement structure is made up of two components. The first component is a strap 22, which runs continuously through the anterior insertion 30, through the outer rim of the body portion 20 and then through the posterior insertion 40 of the device. The strap 22 is made of a material having a high elastic modulus. The strap 22 is a flat piece of stiff yet flexible polymer (such as PEEK or polyethylene), such as a piece of polymeric ribbon or tape. Alternatively the strap 22 may be moulded with a woven or braided fibre structure within it. The second component of the reinforcement structure is a further structural element 23, preferably located within the central portion 11 portion of the body portion 20, different examples of which will be further described below. In the FIG. 3 embodiment, the structural element 23 is shown as a sinusoidal arrangement of fibres. The fibres are preferably polymer fibres, and will be described in more detail below. The structural element 23 may be affixed to, integral with, or separate from the strap 22. The fibres of the structural element 23 may extend from the body portion 20 into both the anterior insertion 30 and posterior insertion 40. The polymer core 24 may extend from the body portion 20 to the anterior and posterior insertions 30, 40. The overmoulding 25 may be present, on the anterior and posterior insertions 30, 40, as well as on the body portion 20.

Referring to FIGS. 4 and 4A to 4C, further embodiments of an FGM structure are shown. FIGS. 4A to 4C show cutaway sections showing detail of possible embodiments of the body portion 20 of the implant device 200 shown in FIG. 4. FIGS. 4A to 4C show cross-sections through the body portion of each embodiment along a radial direction. Referring to FIG. 4A, this shows a body portion 20, which as with the FIG. 3 embodiment, has an overmoulding 25 of a wear-resistant elastomer. Within the overmoulding 25, the main bulk of the body portion 20 is comprised of a core 24. Embedded within the core 24 is a strap 22, which as with the strap 22 in the FIG. 3 embodiment, runs continuously through the anterior insertion 30, through the outer rim of the body portion 20, very close to the outer rim, and then through the posterior insertion 40 of the device. Also embedded within the core 24 is a structural element 23A, comprising elongate fibres. The structural element 23A extends through the body portion 20, along a circumferential direction, and is located within the body portion 20, radially between the strap 22 and the inner rim of the body portion 20. The fibres may be randomly arranged, as in the FIG. 6A embodiment (described below).

FIG. 4B shows an embodiment like that of FIG. 4A, except that the implant device does not have any overmoulding layer over the core 24. An overmoulding layer may not be needed if an elastomer/foam with sufficiently low elastic modulus yet high enough wear-rate constant is used for the material of the core 24, or if the core 24 is made of two elastomers as a single injection casting producing a continuous gradient of material between the outer surface and the inner body for example.

FIG. 4C shows a further embodiment of a body portion. Like the FIGS. 4A and 4B embodiments, the device has a strap 22 extending therethrough, parallel with the outer rim of the body portion 20. In the FIG. 4C embodiment a much higher elastic modulus material with sufficient wear resistance is used as the material of the core 24. One or more cavities 27 are provided within the core 24 to provide radial elastic or shear modulus values similar to the tissues of a natural meniscus. The cavities 27 may be empty (i.e. voids in the material of the core 24) or may contain a low elastic modulus material. The embodiment shown in FIG. 4C has two cavities, which extend in a circumferential direction through the body portion 20.

Figure 5A:
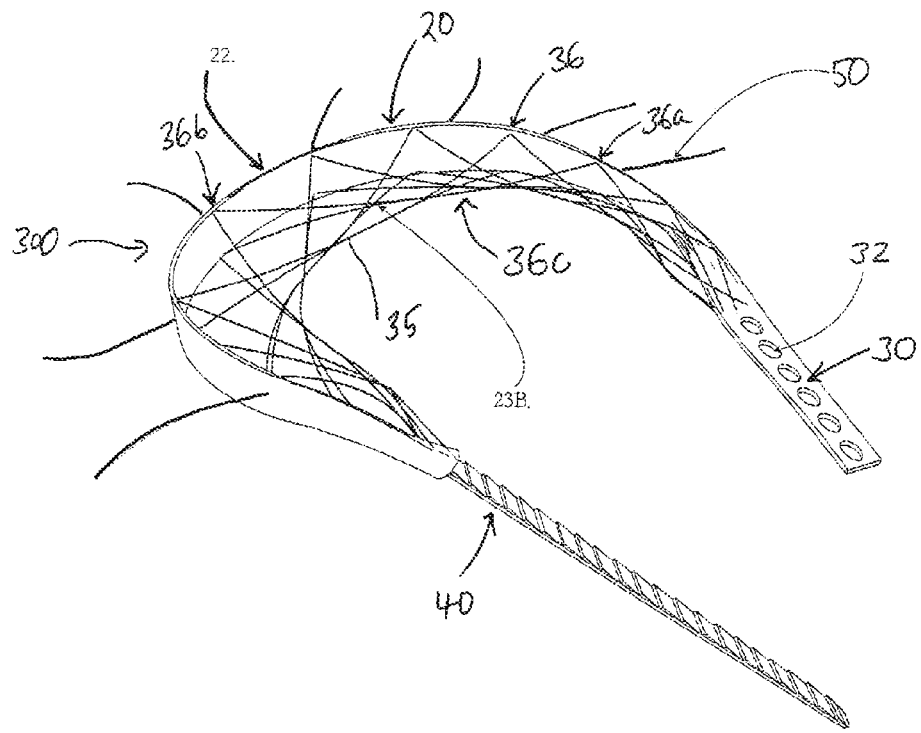
FIG. 5A shows a perspective view of an implant device, with the polymer core material not shown, showing the strap and the reinforcing structure.

Referring to FIG. 5A, this shows a further embodiment of an implant device 300. As with the previous embodiments, a single integral strap 22 continuously extends from the posterior insertion 40, through the body portion 20, and into the anterior insertion 30. The strap 22 provides anchoring points for sutures 50 that exit out of the device body. The sutures 50 may be used to secure the device to surrounding soft tissues. The sutures 50 and structural element 23B may be fabricated as part of the strap 22 or joined to the strap 22 through chemical or mechanical fixation. The sutures 50 may be pre-woven threads to be used as guide wires to assist in the implantation of the implant device during surgery. Alternatively, the implant device may have fixation points for suturing which are designed such that the material of the body portion is pierced and sutures or the like are threaded through said points before being attached to surrounding tissue.

The strap 22 additionally provides an anchoring point for a further structural element 23B located in the body portion 20. The structural element 23B is comprised of a plurality of polymer fibres 35. Each fibre 35 is coupled to the strap 22 at one or more attachment points 36. Preferably each fibre 35 is coupled to the strap 22 at two attachment points 36, first and second attachment points of each fibre being spaced apart from one another along the length the strap 22. The path of each fibre 35 between first and second attachment points 36 (e.g. between attachments points 36a and 36b shown in FIG. 5A) provides a tangent line, the plurality of tangent lines provided by the plurality of fibres effectively providing a curved inner rim 36c of the structural element 23B. This arrangement of fibres creates a high concentration of fibres at the inner rim of the body portion 20, this being an area of the meniscus that is prone to tearing. This arrangement of fibres therefore helps prevent the implant device from becoming torn at the inner rim. The structural element 23B therefore provides shearing stiffness to the implant substantially within the plane of the body portion 20. All or some of the fibres are pre-tensioned between the attachment points. Alternatively, the fibres are not pretensioned but are substantially slack between attachment points.

Each attachment point of a particular fibre may be at the same height on the strap 22 (relative to the top and bottom edges of the strap 22). Alternatively, the attachment points of a particular fibre may be at different heights on the strap. By arranging the fibres such that some attachment points are at or near the top edge of the strap and some attachment points are at or near the bottom edge of the strap and/or some attachment points are at locations between the top and bottom edges of the strap, the fibres 35 provide a reinforcement structure 23B that spans the depth of the body portion 20 between the tibial face and femoral face of the implant device.

Each of the fibres 35 preferably crosses at least one other fibre of the structural element 23B.

The fibres 35 are gathered together such that they extend close to one another at the posterior and anterior ends of the body portion 20, such that there is a high density of fibres where the body portion 20 extends into the posterior and anterior insertions 40, 30 of the device. The fibres 35 may extend substantially along the whole of or a portion of the length of the posterior and anterior insertions 40, 30.

As the body portion 20 of the implant device is compressed by the femur during use, the wedged cross-section of the body portion 20 will be caused to extrude radially, causing the circumference of the device to increase. These compressive loads are transferred into circumferential or "hoop" stresses; tension within the body portion 20 is transferred via the strap 22, into the posterior and anterior insertions 40, 30. The posterior and interior insertions 40, 30 will be fixed to the subject's tissue (as will be described below), therefore the strap 22 transfers forces within the implant device to the subject's tissue. Compressive loads on the implant are also transferred to the fibres 35 of the structural element 23b, any slack between the attachment points of each fibre absorbing the tensile forces. As the body portion 20 stretches, the fibres 35 get closer to one another, the crossovers between the fibres causing the structural element 23b to increase in stiffness as it is stretched.

The fibres 35 may be threadedly coupled to the strap 22 to form each attachment point 36 (e.g. by sewing).

Alternatively the fibres 35 may be adhered to the strap 22 at each attachment point 36, for example using glue.

Instead of having single fibres that are affixed to the strap 22 at one or more attachment points, each fibre may be comprised of more than one constituent fibre, each constituent fibre terminating at an attachment point with the strap 22. The constituent fibres transfer forces exerted on the fibres to the strap 22, which transfers forces from the body portion 20, to the anterior and posterior insertions 30, 40, and to the subject's tissue, via fixation of the anterior and posterior insertions 30, 40, and to the subject's tissue.

The strap 22 and structural element 23B are embedded within the polymeric material of the core (not shown in FIG. 5A).

Figure 5B:
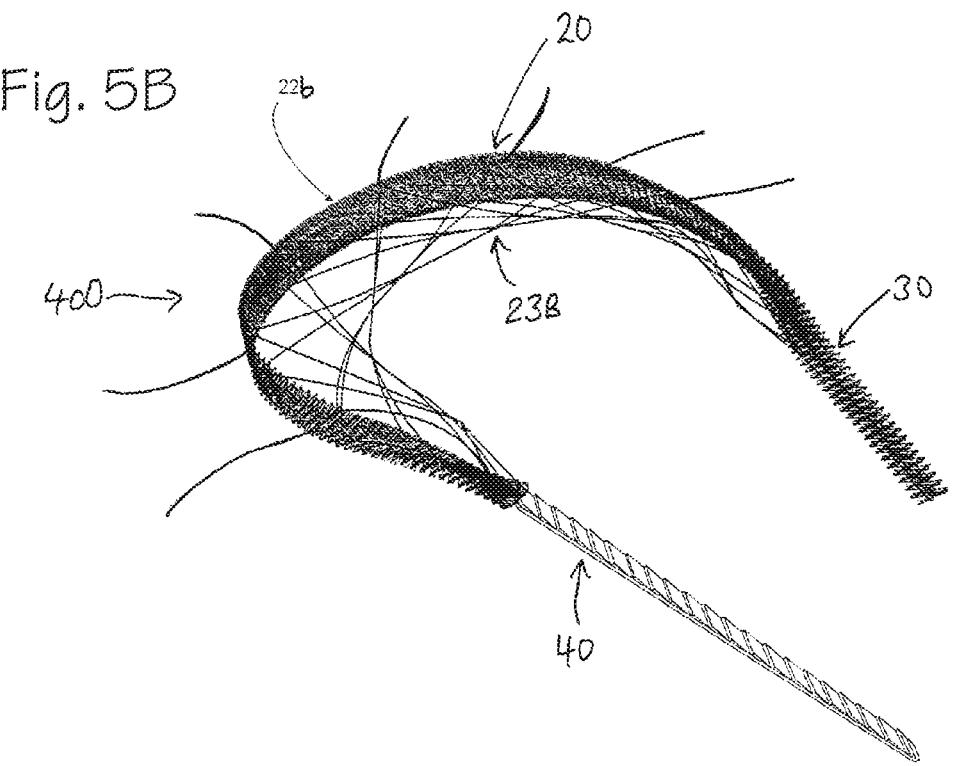
FIG. 5B shows a perspective view of a further embodiment of an implant device, like that of the FIG. 5A embodiment, but having a strap of woven material.

Referring to FIG. 5B, this shows a further embodiment of an implant device 400 like that of the FIG. 5A embodiment, but wherein the strap 22b is formed of woven extruded fibres. The fibres of the strap 22b may be woven in any suitable arrangement. The outer material of the anterior insertion 30 is not shown, such that the woven strap 22b that extends from the body portion 20 and into the anterior insertion 30 is visible in the anterior insertion 30. The strap 22b also extends from the body portion 20 into the posterior insertion 40, however in FIG. 5B, the outer material of the posterior insertion 40 is shown, such that the strap 22b is not visible in the posterior insertion 40.

The strap 22b of the implant device 400 in the FIG. 5B embodiment is made from woven fibres, however it will be understood that the strap could be made from a combination of solid and woven elements.

FIG. 6A to 6F show further embodiments of implant devices, each having a different form of structural element 23 comprising fibres, the fibres of the structural element 23 each having a different geometry/arrangement in each embodiment. Each of the embodiments 6A to 6F has a strap 22, like in the previous embodiments, which extends through the posterior insertion 40, body portion 20 and anterior insertion 30. As a result, the anterior and posterior insertions can be as stiff as possible in axial tension, while also remaining soft enough for a surgeon to bend them and thread them through a tunnel or channel for the purposes of fixation (as described below). In each of FIGS. 6A to 6E, the structural element that is provided in addition to the strap 22 is comprised of a plurality of polymer fibres, which may vary in thickness from 1 µm to 1 mm. In FIGS. 6A to 6F, the strap 22 and structural element are embedded within a polymeric material (not shown in the figures). All of the implant devices of the FIG. 6A to 6F embodiments can be made by rapid prototyping.

Figure 6A:
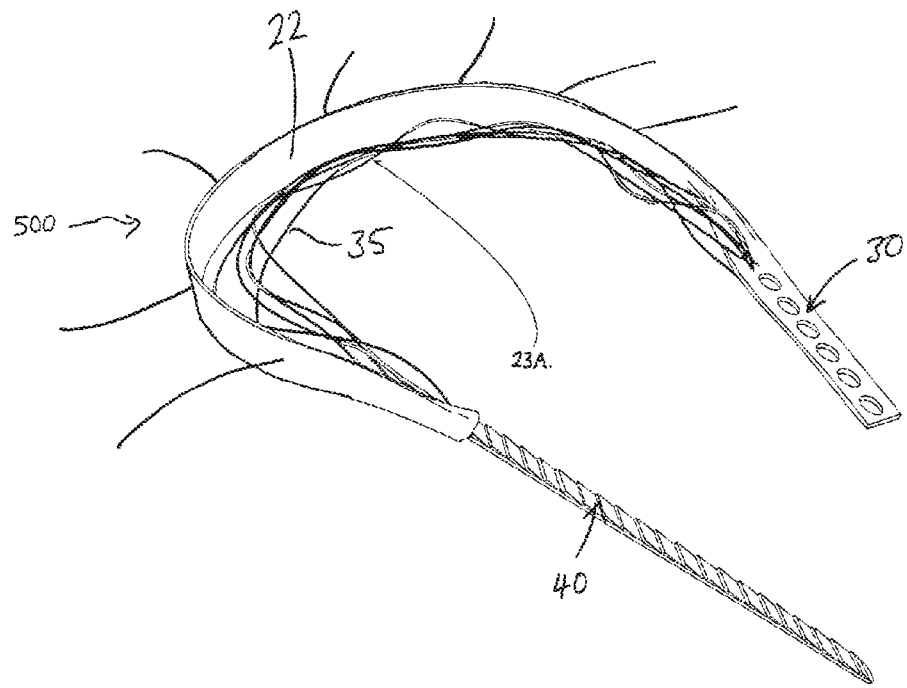
FIGS. 6A to 6F show perspective views of various embodiments of implant devices, with the polymer core material not shown.

The FIG. 6A embodiment is an implant device 500 having a structural element 23A wherein the polymer fibres 35 are substantially randomly arranged. Preferably, the fibres 35 are not coupled to the strap 22. The fibres extend along a direction substantially parallel with the outer rim of the body portion, the fibres crossing over one another along the circumferential path. The fibres are arranged such that each fibre crosses over at least one other fibre. The fibres may extend into the posterior and anterior insertions 40, 30 or may terminate where by the body portion 20 transitions to the posterior and anterior insertions 40, 30. The fibres are designed to be loose when encapsulated, only drawing tight and affecting the elastic modulus of the implant device when the device has undergone a certain level of strain. The criss-crossing fibres in the structural element 23A may be glued together. The fibres in the FIGS. 4A and 4B embodiments may be arranged as in the FIG. 6A embodiment.

Figure 6B:
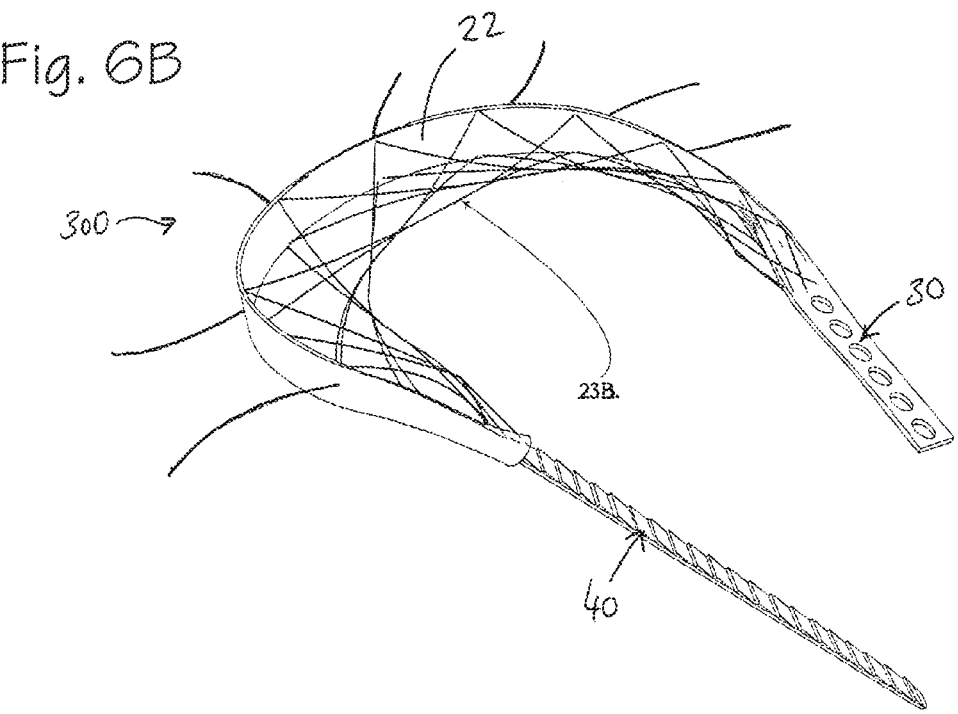

The FIG. 6B embodiment is an implant device 300 wherein the structural element 23b is formed as in the FIG. 5A embodiment, as described above.

Figure 6C:
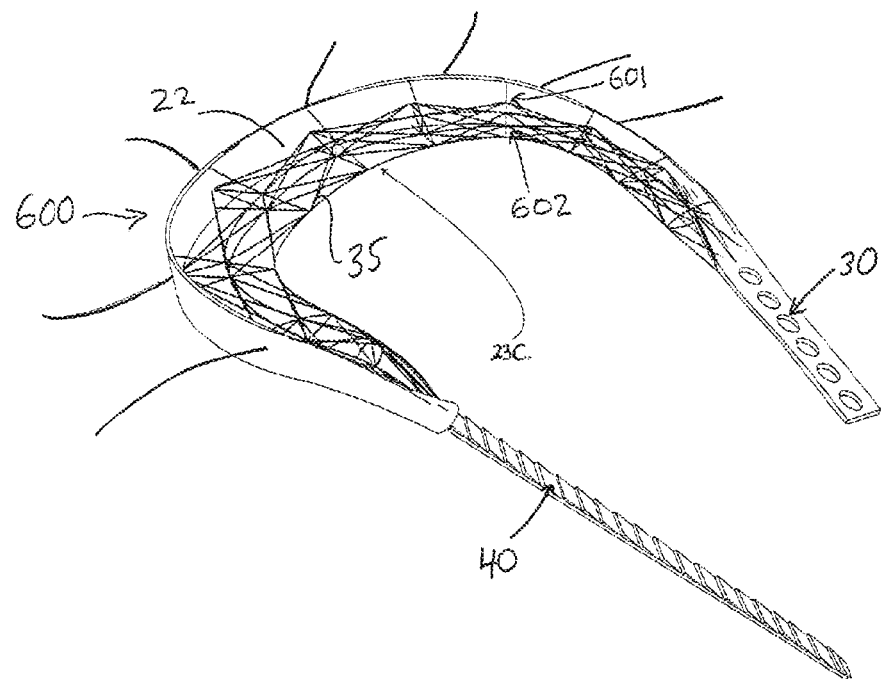

The FIG. 6C embodiment is an implant device 600 that has a structural element 23C which is similar to the structural element 23B of the FIG. 6B embodiment, except that the fibres 35 are each coupled to the strap 22 at more attachment points 36 than in the FIG. 6B embodiment. Each fibre 35 is preferably coupled to the strap at around four attachment points 36, the attachment points 36 of each fibre being spaced along the length of the strap 22 (of course, the fibres could have more or less attachment points). The fibres have axial stiffness against elongation, but are transversely flexible. This arrangement provides a more rigid reinforcing structure than that of the arrangement of fibres in the structural element 23B in the FIG. 6B embodiment. The FIG. 6C structural element 23C has a reinforcing structure involving a cellular structure. By varying elements such as the fibre diameters, the cell sizes or the overall arrangement of fibres, it is possible to design a structure that can elastically deform and reinforce the inner rim of the device. Some of the reinforcing fibres are attached at or close to the upper rim of the outercircumference (e.g. at attachment point 601), while others attach at or near to the lower surface of strap 22 (e.g. at attachment point 602), thus giving a volume of material with fibre reinforcement which has a substantially triangular cross-section, reinforcing close to the upper and lower surfaces of the body, thus protecting the surfaces against tearing.

Figure 6D:
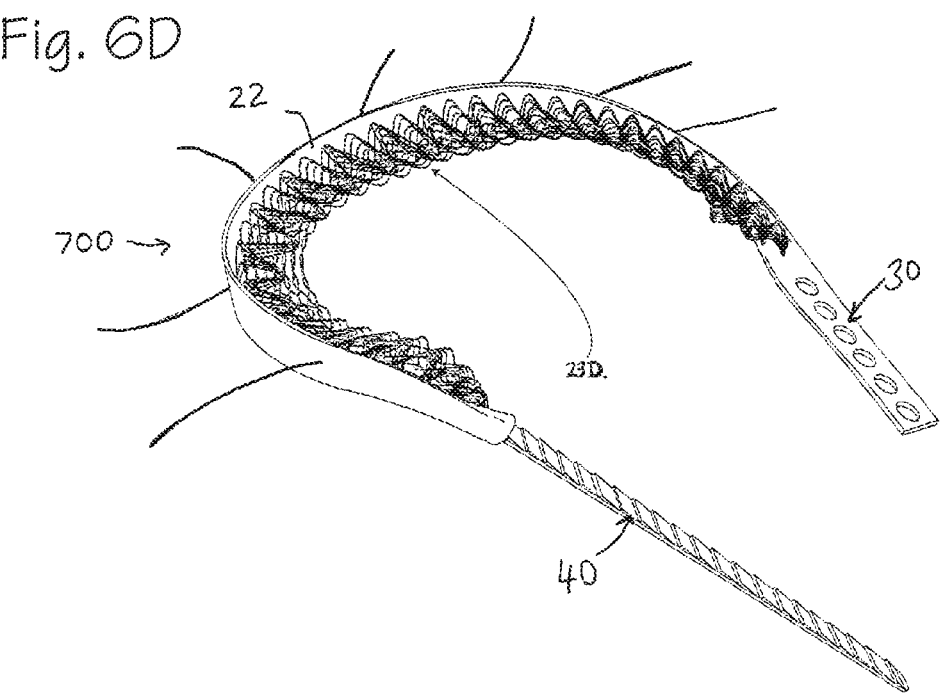

The FIG. 6D embodiment is an implant device 700 that has a structural element 23D comprising a plurality of fibres that are each arranged in a wavelike configuration (e.g. a sinusoidal configuration). The fibres are not under tension when encapsulated in the polymeric matrix of the body portion 20, but can draw tight when the implant device is subjected to tensile forces along a circumferential direction of the device. The sinusoidally arranged fibres may cross over one another. Variation in frequency and orientation of the fibres can be used to affect the properties of the implant device. The sinusoidal arrangement of the fibres gives this implant device embodiment a greater elasticity in the circumferential direction than the other embodiments of FIGS. 6A to 6C. Once implanted, the body portion 20 of the device of the FIG. 6D embodiment can be tensioned using attachment means, as described below, to optimise the elasticity of the device for the subject.

Figure 6E:
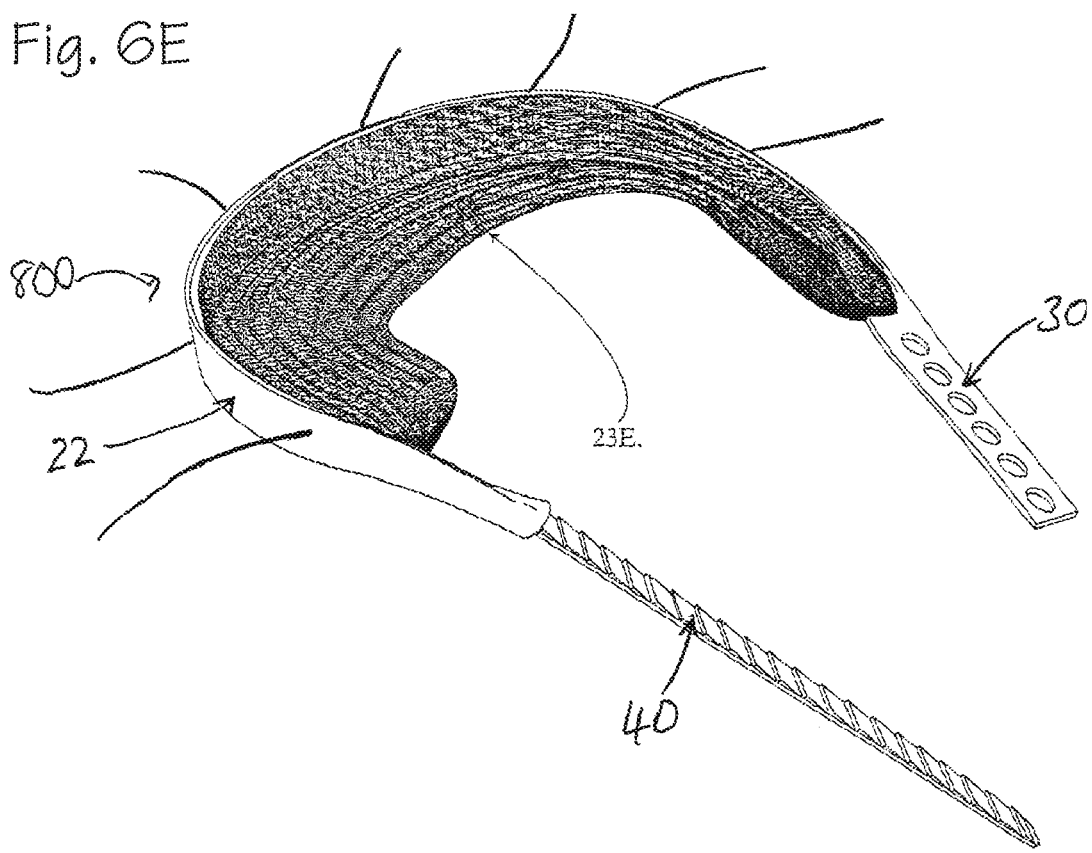

The FIG. 6E embodiment is an implant device 800 that has a structural element 23E made of a three-dimensional woven, braided or knitted structure, which can be constructed or laminated into the body portion 20 of the device. The woven structure 23E can stretch radially and circumferentially, as the implant device is subjected to forces during use.

Figure 6F:
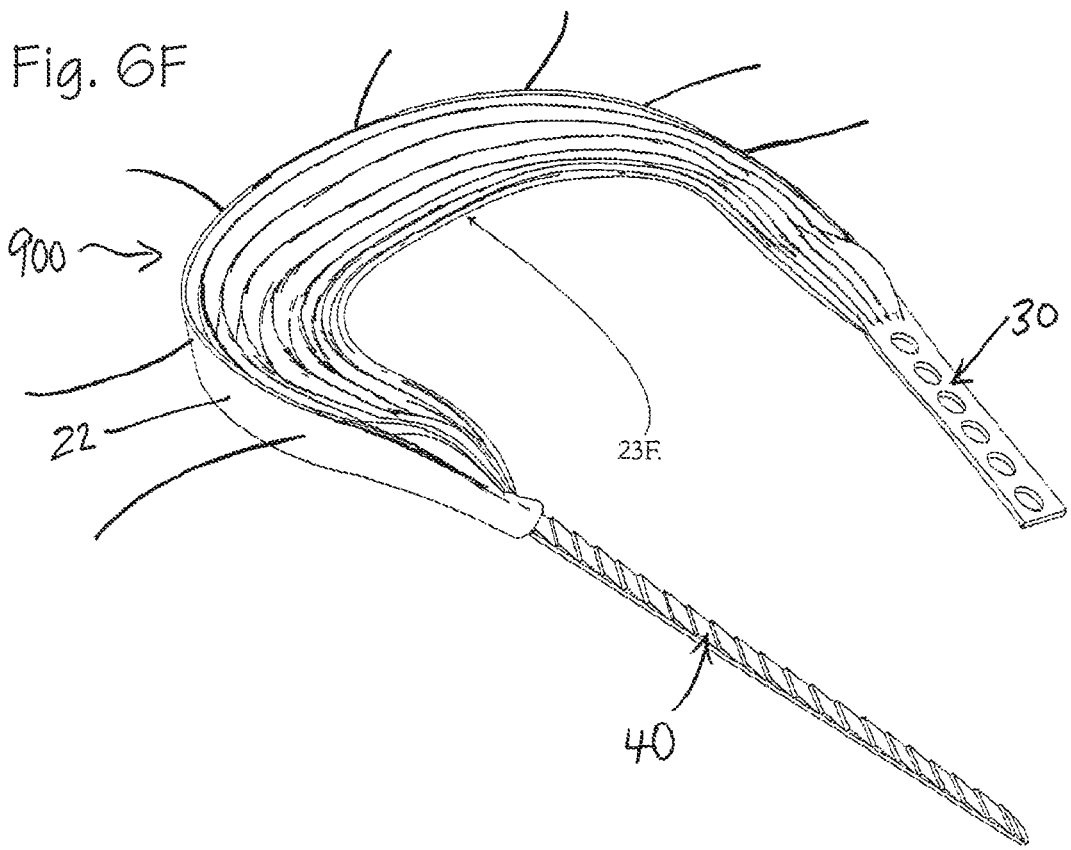

The FIG. 6F embodiment is an implant device 900 that has a structural element 23F comprising electrospun anisotropic polymer sheets that have been folded or laminated into the body portion 20 of the device. The polymer sheets may comprise a plurality of fibres that have been formed into a polymer sheet via the electrospinning process. Control of the electrospinning process enables variations in the fibre orientation to be made throughout each sheet and can be used to control the anisotropy throughout the body portion 20 of the device.

In all of the embodiments shown in FIGS. 6A to 6F, the density of fibres with respect to the body portion volume can be varied in order to vary the properties of the device such as the overall elasticity.

In all of the embodiments described above having a plurality of fibres, the reinforcing fibres can be condensed together within the body portion, as they approach the posterior and anterior ends of the body portion, such that there is a high density of fibres where the body portion 20 extends into the posterior and anterior insertions 40, 30 of the device, to increase the stiffness in this portion of the implant. In this way, the anterior and posterior insertions can be relatively stiff in axial tension, while also remaining soft enough for a surgeon to bend them and thread them through a fixation tunnel or channel as described below. The fibres 35 may extend within all or a portion of the length of the posterior and anterior insertions 40, 30.

Figure 1A:
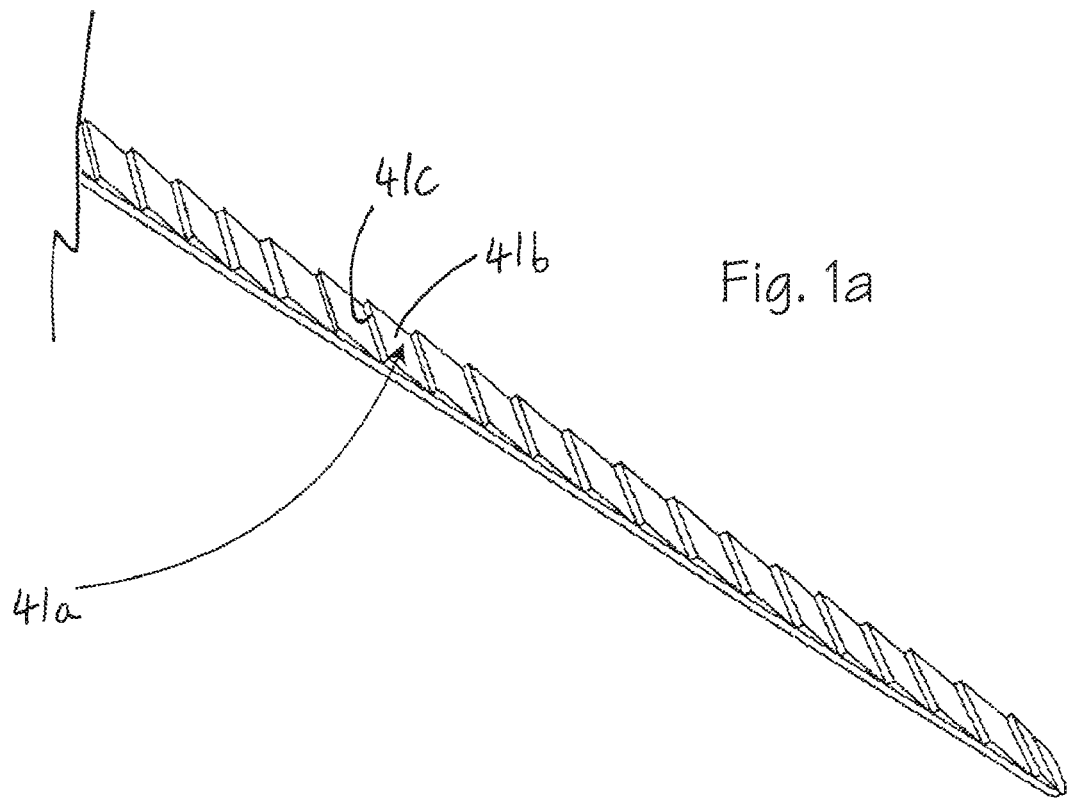
FIG. 1A shows a close-up of the stepped top surface of the posterior insertion of the implant of FIG. 1.
Figure 7:
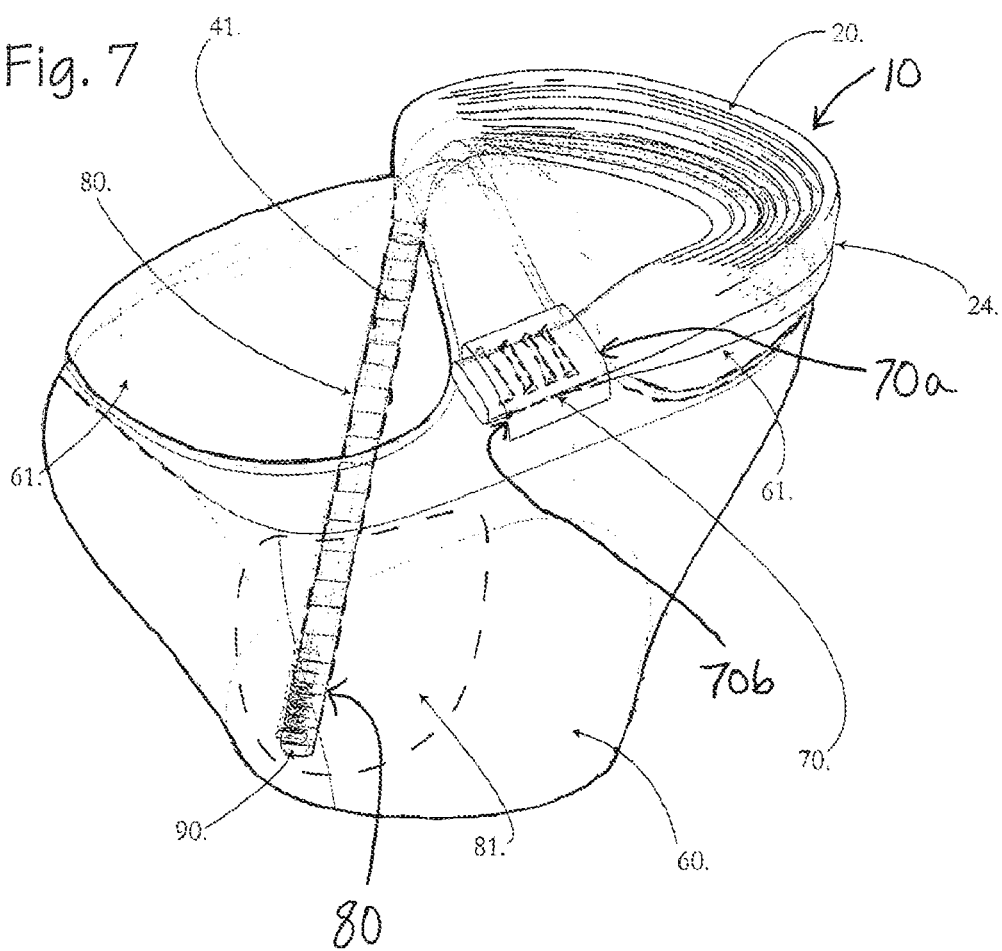
FIG. 7 shows a perspective view of an implant system incorporating an implant device of FIG. 1, shown implanted onto the tibial plateau of a subject, showing the posterior and anterior fixation means.
Figure 8:
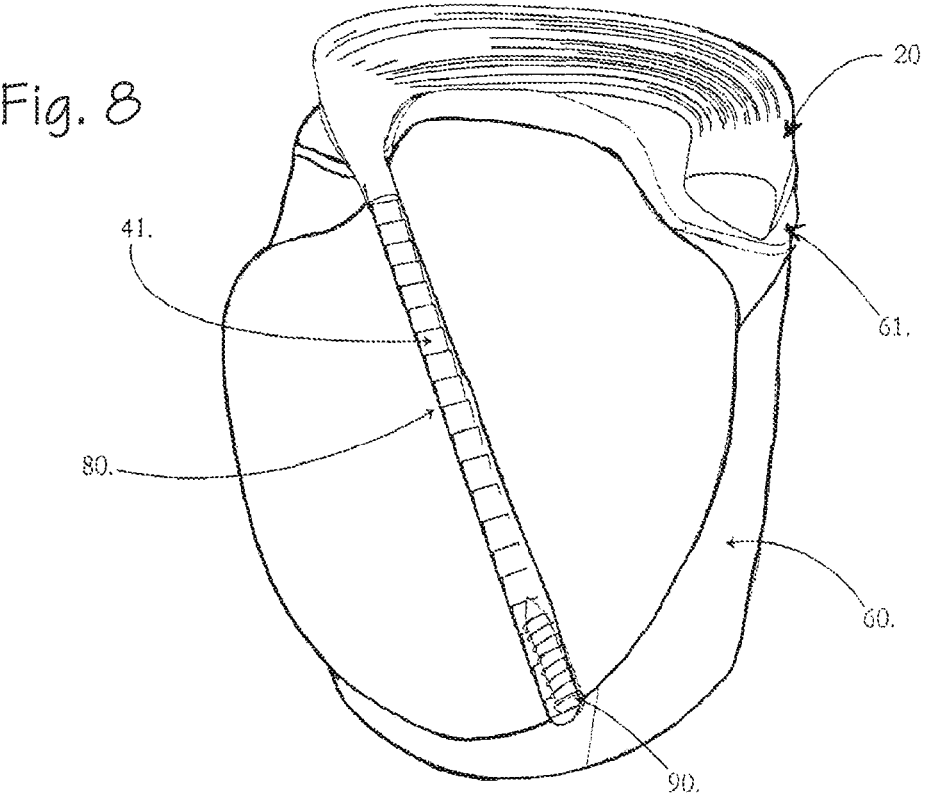
FIG. 8 shows a different perspective view of the system of FIG. 7, with a portion of the tibia shown cutaway to show how fixation of the posterior insertion is achieved.

Referring to FIGS. 1, 7 and 8, possible means for fixation of the device at a subject's joint will now be described. Referring to FIG. 1, the posterior insertion 40 has a stepped top surface 41 (i.e. a serrated or barbed top surface). This stepped top surface 41 forms a plurality of ratchet elements being ratchet teeth 41a on the posterior insertion 40. Referring to FIG. 1A, which shows a close up of the stepped surface 41, each ratchet tooth 41a has a first surface 41b that slopes down towards the posterior insertion 40 in a direction towards the free end of the posterior insertion 40, and a second shorter surface 41c which slopes towards the posterior insertion 40 in a direction away from the free end of the posterior insertion 40, the second surface having a steeper slope than said first surface. The plurality of elements on the posterior insertion 40 for cooperating with corresponding elements on the fixation device (as will be described below) need not be assymetrical teeth, but could of course be any elements, such as those of a symmetrical screw thread form, that will engage in use with one or more corresponding elements on a fixation device.

Referring to FIG. 7, this shows the implant device 10 of an implant system fixed to a tibia 60. The implant device 10 in FIG. 7 is shown installed to replace the lateral meniscus of the knee joint. FIG. 7 shows the relative location of cartilage 61 on the tibial plateau relative to the installed implant device. The posterior insertion 41 is inserted during installation through a tunnel 80 that has been pre-drilled in the subject's tibia 60. The tunnel 80 may be created using a suitable drill guide instrument. The tunnel 80 extends from an opening within the knee, in the posterior of the tibia to an opening in a wide anterior region 81 on the lateral side of the tibia, below the tibial plateau. An interference screw 90 or other suitable fixation device is used to fix the posterior insertion 40 in the tunnel 80. The interference screw preferably has external threading which is adapted to penetrate into bone on either side of the tunnel 80, fixing the interference screw 90 in the tunnel 80 while, at its other side, interlocking with the serrated surface 41 of the posterior insertion 40.

Figure 11:
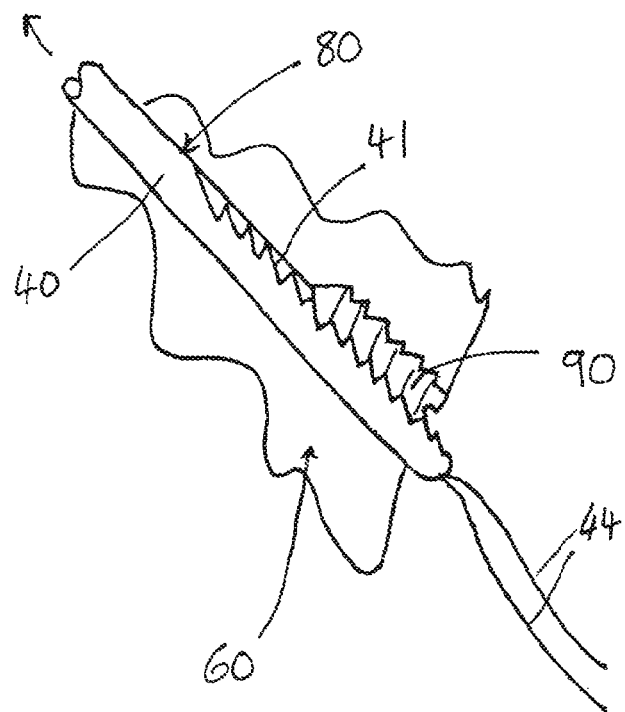
FIG. 11 shows a cross-sectional close-up view along the posterior insertion of FIG. 7.

FIG. 8 shows an alternative view of the posterior fixation through a cutaway of the tibia 60 showing interference screw 90 mated against the stepped surface 41 of the posterior insertion 40. FIG. 11 shows a close-up cross-sectional view through tunnel 80 in the tibia 60, showing how the interference screw 90 mates against the stepped surface 41 of the posterior insertion 40 (only a portion of the posterior insertion 40, adjacent its free end is shown in FIG. 11). In FIG. 11, the posterior insertion 40 has sutures 44 attached at its free end, for use in pulling the posterior insertion 40 down the tunnel 80 during installation.

Figure 1B:
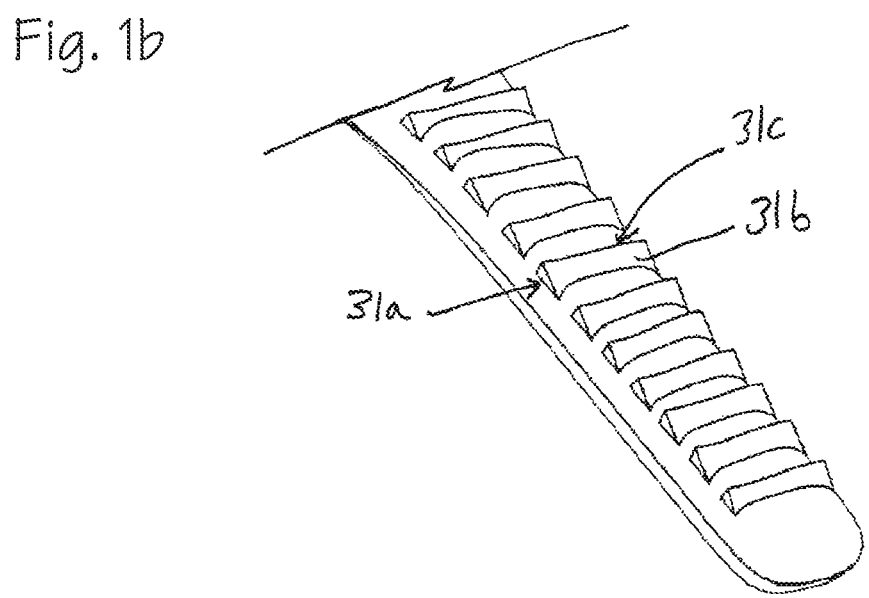
FIG. 1B shows a close-up of the stepped top surface of the anterior insertion of the implant of FIG. 1.

Referring to FIG. 1, the anterior insertion 30 has a stepped top surface 31. This stepped top surface 31 forms a plurality of ratchet elements being ratchet teeth 31a on the posterior insertion 30. Referring to FIG. 1B, which shows a close up of the stepped surface 31, each ratchet tooth 31a has a first surface 31b that slopes down towards the posterior insertion 30 in a direction towards the free end of the posterior insertion 30, and a second shorter surface 31c which slopes towards the posterior insertion 30 in a direction away from the free end of the posterior insertion 30, the second surface having a steeper slope than said first surface.

Referring to FIG. 7, the implant system has a low profile anterior fixation plate 70 to fix the anterior insertion 30 to the tibia. The anterior insertion 30 is strap shaped, akin to a tape, to avoid being prominent where it passes out of the knee. The fixation plate 70 may be screwed or stapled to the bone and is shaped to bridge over the anterior insertion 30 when implanted. For example, the fixation plate 70 may have holes (not shown in the figures), one on each side of the bridging crossbar section, each for receiving a screw to pass through the screw hole and into the bone. The bridging crossbar section forms a channel underneath the fixation plate through which the anterior insertion can be received, when the fixation plate is affixed to the bone. When the fixation plate 70 is fixed to the tibia 60, there is a channel formed between the fixation plate 70 and the bone, the channel having a first open end 70a, facing the body portion 20 of the implant device when installed and a second open end 70b, facing away from body portion 20 of the implant device when installed. The fixation plate 70 has at least one protuberance (not shown in FIG. 7) extending from the underside of the crossbar of the fixation plate 70 (e.g. a serrated underside) to engage the ratchet teeth of the anterior insertion 30 in use. The fixation plate 70 therefore acts as a ratchet, allowing the anterior insertion 30 to be drawn through the channel formed underneath the crossbar of the fixation plate 70, in a direction away from the body portion 20 of the implant device, when the fixation plate 70 is fixed to the bone. However, the ratchet mechanism provided by the fixation plate 70 prevents the anterior insertion 30 from being withdrawn from the fixation plate 70 in a direction towards the body portion of the implant device when installed.

Figure 12:
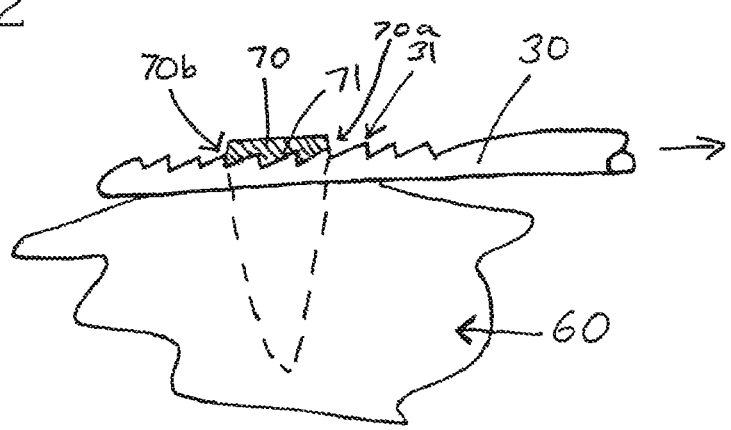
FIG. 12 shows a cross-sectional close-up view along the anterior insertion of FIG. 7.

FIG. 12 shows a cross-sectional view through the anterior insertion 30 of FIG. 7, along the elongate axis of the anterior insertion 30 showing how latching elements on the underside of the fixation plate 70 engage with corresponding cooperating elements on the anterior insertion 30. The underside of the fixation plate 70 has a serrated surface, the serrations corresponding to the shape of the stepped surface 31 of the anterior insertion 30. The serrated underside 71 of fixation plate 70 mates in use against the stepped surface 31 of the anterior insertion 30 (only a portion of the anterior insertion 30, adjacent its free end, and only a portion of tibia 60 is shown in FIG. 12). This provides a ratchet mechanism allowing the anterior insertion 30 to be drawn through the channel formed underneath the crossbar of the fixation plate 70, in a direction away from the body portion 20 of the implant device but preventing the anterior insertion 30 from being withdrawn from the fixation plate 70 in a direction towards the body portion of the implant device when installed.

During installation of the implant device, firstly a tunnel 80 is drilled in the subject's tibia, the tunnel extending from an opening in the posterior of the tibia to an opening in a wide anterior region 81 on the lateral side of the tibia. The posterior insertion 40 is passed into the knee through a small arthroscopy portal, and then passed around and under the femoral condyle, and then inserted in the tunnel 80 via the posterior opening of the tunnel 80. The posterior insertion 40 is preferably sized such that its free end extends out of the anterior opening of the tunnel 80 when the posterior insertion 40 is fully inserted in the tunnel 80. Alternatively, the posterior insertion 40 is preferably sized such that its free end is at/near the anterior opening of the tunnel 80 when the posterior insertion 40 is full inserted in the tunnel 80. The posterior insertion helps to pull the body portion into the knee, and around the femoral condyle. The interference screw 90 is inserted in the anterior opening of the tunnel 80 such that it engages with the posterior insertion 40, as shown in FIG. 7. The interference screw 90 also engages with the tunnel wall, creating a mechanical fixing, fixing the screw 90 and posterior insertion 40 relative to the tunnel. When the posterior insertion 40 has been inserted in the tunnel 80, the ratchet teeth 41a of the posterior insertion 40 allow the threaded screw 90 to be inserted from the anterior opening of the tunnel, but the ratchet teeth 41a resist the posterior insertion from being withdrawn from the tunnel 80 via the posterior opening of the tunnel 80, by means of the ratchet teeth 41a engaging with the threads of the fixed interference screw 90. The ratchet teeth 41a and the engagement of the interference screw 90 in the bone prevent the screw 90 from being withdrawn from the tunnel 80 via the anterior opening.

Once the posterior insertion 40 has been fixed to the subject's bone, the anterior insertion 30 is fixed to the subject's bone using the fixation plate 70. The fixation plate 70 is fixed to the bone via suitable means as described above (e.g. using screws or staples). The free end of the anterior insertion 30 can be inserted into the channel formed under the fixation plate 70 via the first open end 70a, and pushed under the fixation plate 70 until the free end of the anterior insertion 30 exits via the second open end 70b. Once the free end of the anterior insertion 30 is accessible, the free end can be pulled through the channel of the fixation plate.

Alternatively, the anterior insertion 30 can be pushed through the channel of the fixation plate, the anterior insertion 30 being sufficiently stiff to be pushed through without buckling. The ratchet mechanism formed between the stepped surface 31 of the anterior insertion 30 and the fixation plate allows the anterior insertion to be drawn through the channel under the fixation plate in a direction facing away from the body portion 20 of the implant device, but prevents the anterior insertion from being withdrawn from the fixation plate in a direction towards the body portion 20 of the implant device. The ratchet mechanism therefore prevents the anterior insertion 30 from detaching from the subject's bone.

The fixation means for the anterior insertion therefore may additionally act as a ratchet allowing tensioning once the posterior insertion is fixed. Once the posterior insertion 40 has been secured as described above, the anterior insertion 30 can be secured to a tensiometer and the tension adjusted to obtain a snug fit around the femoral condyle. The anterior insertion will stop being drawn through the fixation plate by the surgeon once the desired tensed configuration has been achieved. The anterior insertion 30 will initially comprise sufficient length such that the free end of the anterior insertion 30 is easily accessible once it has passed through the channel of the fixation plate. The anterior insertion 30 preferably comprises excess length in order to allow correct tightening of the device during implantation. Any excess length of the anterior insertion 30 can be cut away once the desired fixation/tension has been achieved. Whereas the anterior insertion 30 of the implant device shown in FIG. 1 has a rounded free end, the free end of the anterior insertion shown in FIG. 7 has a square end, the excess length of the anterior insertion having been cut away.

As shown in FIG. 11, either or both of the posterior and anterior insertions may have sutures 44 attached to the free end (e.g. in the form of a loop or tape), made of strong material. The sutures may protrude from the end of the moulding of the posterior and/or anterior insertion. The sutures aid implantation by providing something that the surgeon can grasp and pull when implanting, for example being useful in pulling the posterior insertion 40 through the bone tunnel. The sutures 44 are suitably thin and soft, for easy handling/knot tying.

Once the posterior and anterior insertions 40, 30 have been fixed to the subject, if the installer wishes to increase the tension within the implant device, the installer can draw the anterior insertion 30 further through the channel of the fixation plate, by pushing the anterior insertion, of pulling on the free end of the anterior insertion 30, until the desired tension has been achieved. It is desirable to initially install the implant device such that it is not over-tense.

Subsequently, if it is desired to increase the tension in the device, or the implant device has become loose over time, the ratchet mechanism provided by the fixation plate can be used to increase the tension on the device.

Preferably the interference screw 90 will have external helical threads, which help the screw to engage with the bone of the tunnel 80 wall. However, it will be understood that the screw may have suitable protuberances, other than helical threads, to engage with the stepped surface 41 of the posterior insertion 40.

The posterior insertion 40 may be moulded with stiffer reinforcements, at least at the portion where it is intended to engage with the interference screw 90. For example, the posterior insertion may be reinforced by the extension of the fibres of the structural element 23, 23A, 23B, 23C, 23D, 23E, 23F from the body portion of the implant device into the posterior insertion 40, reaching the portion of the posterior insertion that is intended to engage with the interference screw 90.

In addition to the use of the stepped surface 41 and interference screw 90 to secure the posterior insertion 40 to the subject's bone, the posterior insertion may also include a plurality of holes through the posterior insertion (not shown in the figures), one of which could be engaged by a screw or cross-pin passing through, into the bone at one or both sides.

When the implant device 10 is fixed as described above, the body portion 20 of the implant device remains relatively free, much like the natural meniscus, with its fixation occurring at the extremes of the insertions 30,40. The fixation means for the anterior insertion 30 effectively secures the anterior insertion to the tibial plateau, recognising that the anterior attachment is close to the anterior edge of the tibial plateau in the natural meniscus.

Figure 9:
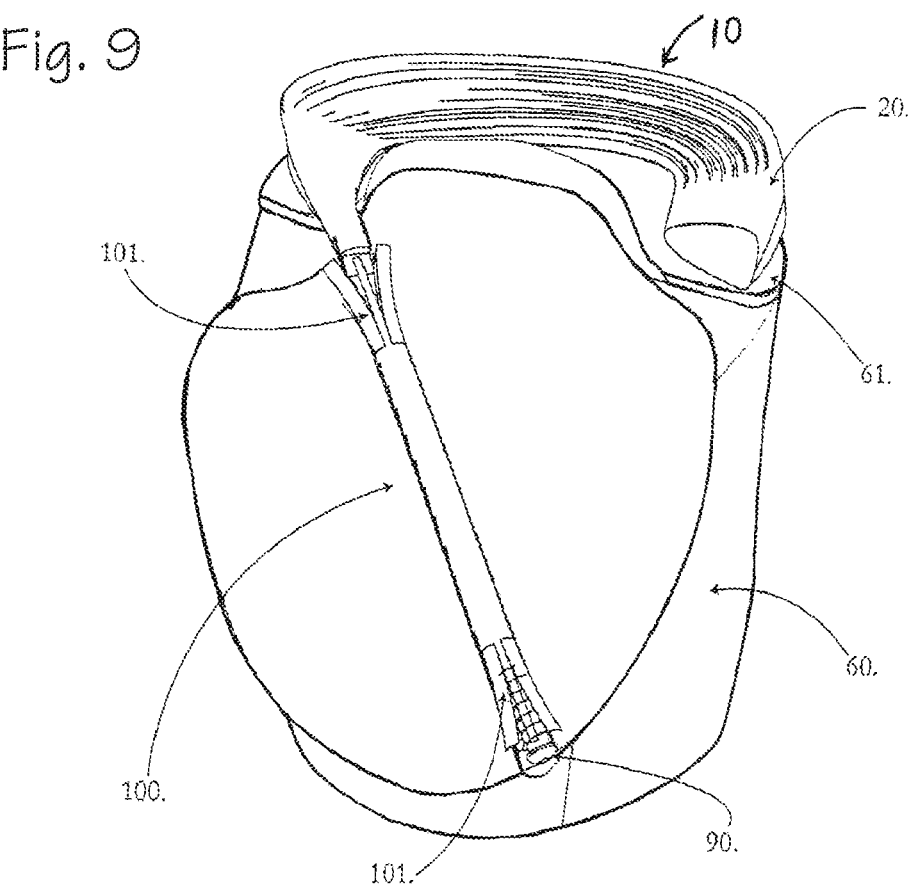
FIG. 9 shows a close-up perspective view of an implant system similar to that of FIG. 7, the system further including a sheath, the system shown implanted onto the tibial plateau of a subject, a portion of the tibia shown cutaway to show how fixation of the posterior insertion is achieved.

Referring to FIG. 9, this shows an alternative posterior fixation means for the implant device 10. In FIG. 9, the anterior end of the body portion 20 of the implant device is shown cutaway to show the cross-sectional shape of the body portion. FIG. 9 shows a cutaway through the tibia 60, showing a sheath 100 having been inserted in the tunnel 80. The sheath 100 is used in order to allow for easy exchange of the implant device without the need for re-drilling, for example if the material of the implant device has worn away.

The sheath 100 is a hollow, elongate member that is tubular in shape. In the FIG. 9 embodiment, the sheath has expanding ends 101 at each end of the sheath (although it will be understood that a sheath without expanding ends could be used). In this embodiment, each end of the sheath 100 has two or more longitudinal cuts, the cuts preferably being spaced around the circumference of the sheath. The cuts are of an appropriate length to allow the ends 101 of the sheath to flare/expand. The sheath 100 preferably has a length that roughly matches the length of the tunnel 80. When the sheath 100 is inserted in the tunnel 80, the expanded ends 101 of the sheath 101 push against the cortical bone near the tunnel apertures (rather than pushing against the soft cancellous bone towards the mid-section of the tunnel 80). The expanded ends of the sheath 101 are caused to flare apart at the top, by pulling of the tapered posterior insertion 40 into the sheath 100, and at the bottom end by the insertion of screw 90.

The sheath 100 may have an outer surface texture and/or bioactive coatings (such as hydroxyapatite) to promote bone ingrowth. The sheath 100 may have a threaded internal surface matching that of the interference screw 90.

During installation, the sheath 100 is inserted in a tunnel 80 that has been pre-drilled in the subject's tibia. Preferably the sheath 100 is inserted from the anterior tunnel aperture, the ends 101 expanding in use. The ends 101 expand against the cortical bone near the tunnel entrances, fixing the sheath against the bone. The posterior insertion 40 is inserted in the tunnel 80 via the sheath end at the posterior of the tibia. The interference screw 90 is inserted in the end of the sheath at the anterior of the tibia and engages with the internal sheath wall, creating a mechanical fixing, fixing the screw and posterior insertion relative to the sheath, which is in turn fixed relative to the bone. In embodiments in which the sheath 100 has internal threading matching that of the interference screw 90, this helps lodge the screw 90 within the sheath 100.

Figure 10A:
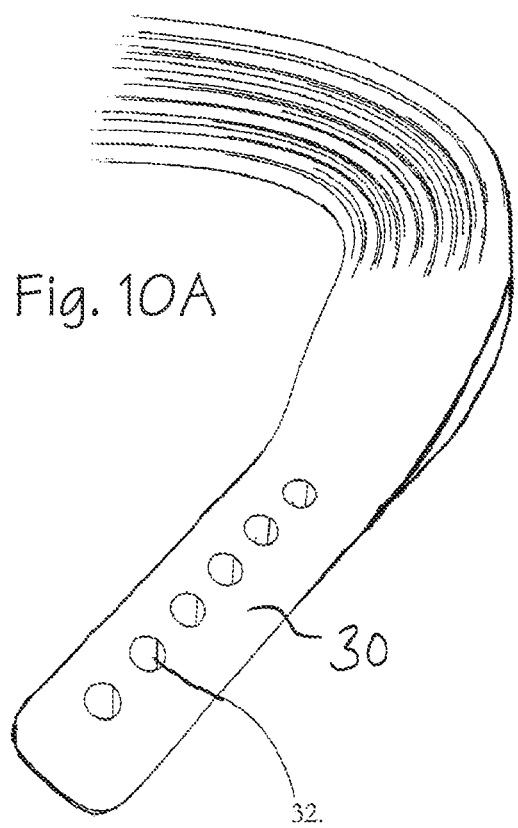
FIG. 10A shows a perspective view of the anterior insertion of the embodiments of FIG. 3, 5A or 6A to 6F, the anterior insertion having a plurality of pre-formed holes for mating with a screw fixator, to fix the anterior insertion to the subject's tissue.

Referring to FIG. 10A, this shows an alternative embodiment of the anterior insertion 30', like that shown in FIGS. 5A and 6A to 6F. Instead of having a stepped top surface 31, the anterior insertion 30' has a plurality of apertures 32 regularly spaced along its length. A screw fixing (not shown) can be used to directly fix the anterior insertion to the outer surface of a subject's tibia. During installation, once the posterior insertion has been fixed, tension will be applied to the anterior insertion 30 until the implant device is at a desired tension, and a screw fixing (or other suitable fixing) will be passed through one of the apertures 32, and driven into the subject's tibia. For example, a cortical screw could be used as the fixing, to fix the anterior insertion to the anterior edge of the subject's tibial plateau. By providing a plurality of apertures 32, the installer can insert the screw fixing into an aperture 32 that overlies a suitable part of the subject's tibia to drive the screw fixing into, once the implant device has been extended to its desired tension. In this embodiment, the anterior insertion is therefore directly fixed to the subject's tissue. Similarly, the posterior insertion 40, instead of having a stepped top surface 41, may have a plurality of apertures (not shown in the figures), regularly spaced along its length. A screw or other suitable fixing could be used to directly fix the posterior insertion 40 to the subject's body. By providing a plurality of apertures along the length of the anterior and/or posterior insertions 30, 40, a desired tension can be exerted on the implant device when installed.

In an alternative means for fixation of the anterior insertion shown in FIG. 10A, a fixation plate may be used (not shown in the figures). As with the FIG. 7 embodiment, the fixation plate has a bridging crossbar section and side portions, each of which can be fixed to the subject's tibia via suitable fixation means (such as screws or staples). The bridging crossbar section forms a channel underneath the fixation plate through which the anterior insertion can be inserted, when the fixation plate is affixed to the bone. The fixation plate may be similar to that of the FIG. 7 embodiment, except that it has a spike or tooth extending from the underside of the crossbar of the fixation plate, adapted and shaped to engage with the apertures 32 in the anterior insertion 32. The spike or tooth may be angled relative to the direction of insertion of anterior portion 30' such that the fixation plate and anterior portion 30' with plurality of holes acts as a ratchet, allowing the anterior insertion 30' to be drawn through the channel formed underneath the crossbar of the fixation plate in a direction facing away from the body portion of the implant, but with engagement of the spike or tooth of the fixation plate 70 in one of the holes of the anterior insertion 30' preventing the anterior insertion 30' from being withdrawn from the fixation plate 70 in a direction towards the body portion of the implant device when installed. In this way, once the implant device has been installed in place on a subject's tibia, and its posterior and anterior ends fixed to the bone, if the installer wishes to increase the tension on the implant device, the installer can pull on the free end of the anterior insertion 30', drawing the apertured anterior insertion through the ratchet-like mechanism of the fixation plate until the desired tension is achieved.

Figure 10B:
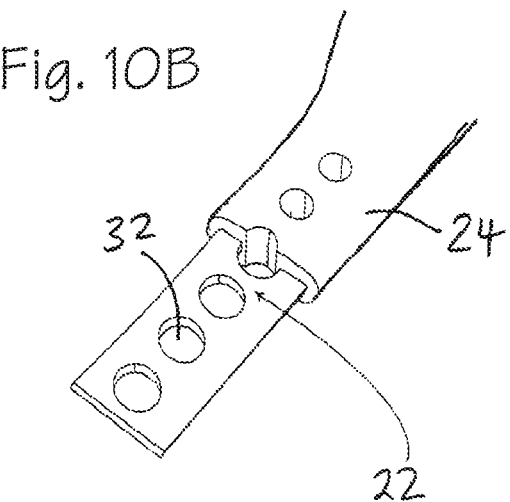
FIG. 10B shows a close-up view of the anterior insertion of the FIG. 10A embodiment, showing the outer polymer core material cutaway, and showing the strap that is embedded within the anterior insertion, with the pre-drilled holes extending through the polymer matrix and the strap.

FIG. 10B shows a close-up view of the anterior insertion 30' of FIG. 10A, showing the core material 24 that encases the strap 22 partially cutaway, and showing the strap 22 that is embedded within. The apertures 32 extend through the core material 24 and the strap 22, to provide maximum transfer of the shear forces from the implant device to the bone. Where a screw or similar fixing is used to directly fix the anterior insertion 30 to the bone, mitigation of stress concentration is achieved between the screw fixing (not shown) and the implant device. The reinforcing fibres (as described above in relation to FIGS. 3-6) may be arranged to encircle the holes, thus strengthening them.

In an alternative means for fixation of the anterior insertion, a tunnel may be drilled for securely receiving the anterior insertion 30, the tunnel being similar to the tunnel 80 for the posterior insertion shown in FIG. 7, also exiting the tibia below the tibia plateau. The anterior insertion will be secured to the tunnel similarly to the posterior insertion in the FIG. 7 embodiment. In embodiments where both the posterior and anterior insertions pass through bone tunnels to similar places on the surface of the tibia, then the two ends of the anterior and posterior insertions may be folded over each other and secured by a single fixation means, such as a buckle or staple, onto the surface of the tibia. The fixation means may include two sets of ratchet means, one for engaging a stepped surface 31 of the anterior insertion 30 and one for engaging a stepped surface 41 of the posterior insertion 40, for tensioning the anterior and posterior insertions relative to the fixation means in use. The ratchet means may be ratchet-like teeth on the underside of the buckle, the sloping surfaces of each ratchet means facing in opposite directions.

Figure 13:
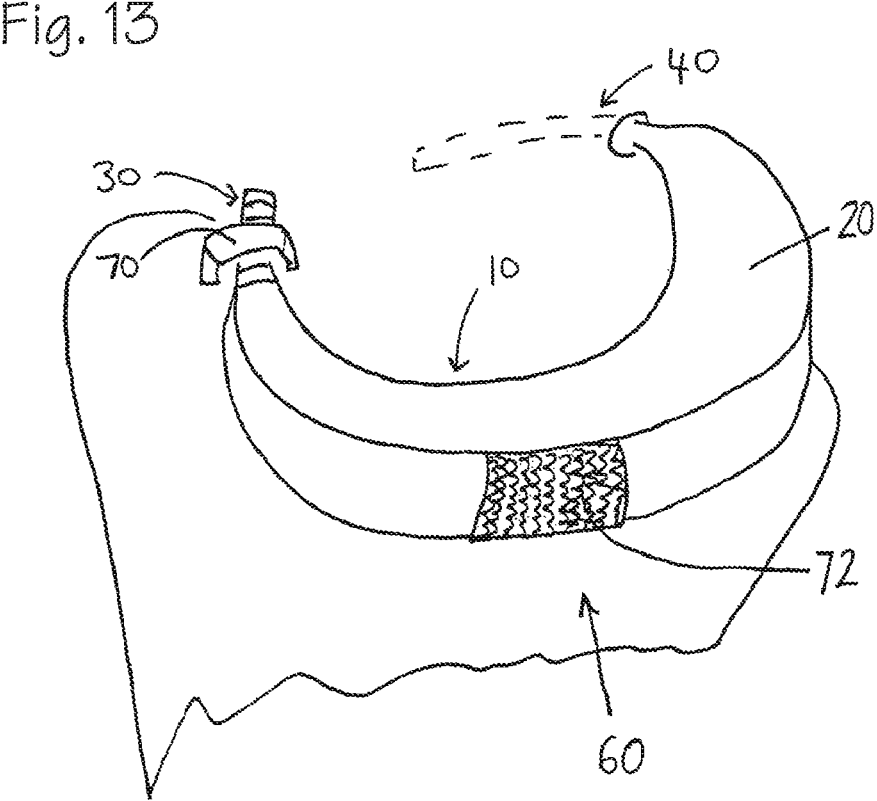
FIG. 13 shows a perspective view of an implant device having a velour patch on a portion of the surface of the outer rim of the body portion.

FIG. 13 shows an implant device 10, with the body portion of the device installed on a subject's tibia 60, the implant device 10 having a velour patch 72 located on a portion of the surface of its outer rim. The velour patch 72 provides a tissue ingrowth zone for peripheral fixation of the device. This allows the implant device to attach to the medial collateral ligament for example.

The function of the meniscus implant depends on the location of the fixation to the tibia. Detailed coordinates of recommended attachment points for the implant device can be provided, in relation to arthroscopically-identifiable bony landmarks, and similar dimensions which could be used in a surgical navigation or robotically-guided system. These dimensions will inform the design of 'offset' drill guides akin to those used in ligament surgery, such that the guide locates on the prominent bony landmark and the guide ensures that the tunnel for the meniscus fixation is positioned at the correct offset away from it, in the anatomical attachment area.

Before installation of an implant device as described herein the installer/surgeon must initially decide on the correct implant size to use. The implant devices described herein can be manufactured in a range of sizes. The implant devices can be supplied in a kit including a range of sizes to select from. Alternatively, the implant device can be custom-designed for a particular subject using MRI-based CAD-CAM. This can be done for example by modifying the size in one or more dimensions. The implant device can be supplied with a patient specific implantation plan, for implementation using surgical navigation, robotic assistance or patient specific drill guides.

In all of the embodiments described herein the strap 22, 22B can extend through substantially the full circumferential length of the implant device (i.e. it can extend without break from a point at or near the free end of the posterior insertion, through the body portion, and through to at or near the free end of the anterior insertion, extending along a circumferential path through the implant device).

As described above, the posterior and anterior insertions are preferably as stiff as possible in axial tension, while also remaining soft enough for a surgeon to bend them and thread them through a fixation tunnel or channel as described below. This allows for strong fixation of the implant device, and eliminates or reduces micromotion between the fixation and the surrounding bone.

Further advantages of the present invention include provision of an implant device capable of generating variations in surface texture as a result of its structure as a means to achieve positive interactions with surrounding tissues.

When implanted at the knee, the implant device of the present invention is unicompartmental, in that the device is adapted for implantation into a compartment defined by the space between the tibial plateau and the femoral condyle. Thus, the device is suited for use in either a lateral compartment or a medial compartment of the knee. Where it is necessary to replace menisci in both compartments, two implant devices according to the present invention could be used.

While the embodiments described above have addressed the meniscus at the knee by way of example, this technology may also be applied to other sites within the human body, such as the glenoid or acetabular labrum, temporomandibular joint or triangular fibrocartilage of the wrist, with appropriate alterations of the geometry, material properties and tissue attachment means. In particular, the acetabular or glenoid labrum may require multiple attachment/fixations means, around the periphery.

The invention claimed is:

1. A prosthetic meniscus implant device for implantation at a knee joint, the prosthetic meniscus implant device comprising:
    a crescent-shaped body portion having an upper surface for engagement with a patient's femur, an opposing lower surface for engagement with a patient's tibia, a first end, a second end, and an arcuate outer rim extending from the first end to the second end,
    a first elongate member extending from the first end of the body portion and terminating in a free end, at least a portion of the first elongate member being strap-shaped or substantially crescent shaped in cross-section,
    a second elongate member extending from the second end of the body portion and terminating in a free end, at least a portion of the second elongate member being strap-shaped or substantially crescent shaped in cross-section,
    a reinforcing element, which extends continuously through the first elongate member, through the body portion, and through the second elongate member, the reinforcing element being a planar, strap-shaped element, and
    a structural element comprising a plurality of fibres embedded within the body portion,
    the implant device being made from a functionally graded material, having at least one mechanical property that varies in a radial direction relative to the crescent-shaped body portion and/or in a circumferential direction relative to the crescent-shaped body portion, wherein the reinforcing element is characterized by a planar face, and the body portion is characterized by a transverse plane corresponding to a transverse plane of the knee joint, and the planar face of the reinforcing element is disposed within the body portion substantially perpendicular to the transverse plane of the body portion, wherein the first elongate member is insertable in a bone tunnel in a subject's tibia and the second elongate member is secureable to the subject's tibia, wherein the body portion has a high tensile stiffness along an axis substantially parallel with the arcuate outer rim of the body portion of less than 2 GPa, and a low shear stiffness in a plane substantially transverse to the outer rim of the body portion of less than 50 MPa.

2. An implant device according to claim 1, wherein each of the fibres extends through the first elongate member, through the body portion of the implant device, and through the second elongate member.

3. An implant device according to claim 1, wherein each of the fibres is coupled to the reinforcing element at at least one point along the length of said fibre.

4. An implant device according to claim 1, wherein the body portion has an elastic modulus gradient, the elastic modulus varying spatially within the body portion.

5. An implant device according to claim 4, wherein the elastic modulus increases in a radial direction, towards the arcuate outer rim of the body portion.

6. An implant device according to claim 4, wherein the elastic modulus increases in a circumferential direction towards the free ends of the first and second elongate members.

7. An implant device according to claim 4, wherein the elastic modulus increases towards an outer surface of the body portion.

8. An implant device according to claim 1, wherein: the second elongate member is insertable in a bone tunnel in the subject's tibia.

9. A prosthetic meniscus implant device for implantation at a knee joint, the prosthetic meniscus implant device comprising:
a crescent-shaped body portion having an upper surface for engagement with a patient's femur, an opposing lower surface for engagement with a patient's tibia, a first end, a second end, and an arcuate outer rim extending from the first end to the second end,
a first elongate member extending from the first end of the body portion and terminating in a free end, at least a portion of the first elongate member being strap-shaped or substantially crescent shaped in cross-section,
a second elongate member extending from the second end of the body portion and terminating in a free end, at least a portion of the second elongate member being strap-shaped or substantially crescent shaped in cross-section,
a reinforcing element, which extends continuously through the first elongate member, through the body portion, and through the second elongate member, the reinforcing element being a planar, strap-shaped element, and
a structural element comprising a plurality of fibres embedded within the body portion,
the implant device being made from a functionally graded material, having at least one mechanical property that varies in a radial direction relative to the crescent-shaped body portion and/or in a circumferential direction relative to the crescent-shaped body portion,
wherein the reinforcing element is characterized by a planar face, and the body portion is characterized by a transverse plane corresponding to a transverse plane of the knee joint, and the planar face of the reinforcing element is disposed within the body portion substantially perpendicular to the transverse plane of the body portion,
wherein the first elongate member is insertable in a bone tunnel in a subject's tibia and the second elongate member is secureable to the subject's tibia,
wherein the body portion has a circumferential tensile stiffness modulus of greater than 50 MPa and a transverse shear stiffness modulus of less than 50 MPa.

10. An implant device according to claim 9, wherein each of the fibres extends through the first elongate member, through the body portion of the implant device, and through the second elongate member.

11. An implant device according to claim 9, wherein each of the fibres is coupled to the reinforcing element at least one point along the length of said fibre.

12. An implant device according to claim 9, wherein the body portion has an elastic modulus gradient, the elastic modulus varying spatially within the body portion.

13. An implant device according to claim 12, wherein the elastic modulus increases in a radial direction, towards the arcuate outer rim of the body portion.

14. An implant device according to claim 12, wherein the elastic modulus increases in a circumferential direction towards the free ends of the first and second elongate members.

15. An implant device according to claim 12, wherein the elastic modulus increases towards an outer surface of the body portion.

16. An implant device according to claim 9, wherein:
the second elongate member is insertable in a bone tunnel in the subject's tibia.

* * * * *